United States Patent [19]

Pirkle et al.

[11] Patent Number: 5,422,004
[45] Date of Patent: Jun. 6, 1995

[54] HIGH PERFORMANCE CHIRAL SELECTOR

[75] Inventors: William H. Pirkle, Champaign; Christopher J. Welch, Northbrook; William E. Bowen, Urbana; Qing Yang, Champaign, all of Ill.

[73] Assignee: Research Corporation Technologies, Inc., Tucson, Ariz.

[21] Appl. No.: 127,931

[22] Filed: Sep. 27, 1993

Related U.S. Application Data

[62] Division of Ser. No. 902,616, Jun. 23, 1992, Pat. No. 5,290,440.

[51] Int. Cl.$^6$ .............................................. B01D 15/08
[52] U.S. Cl. ............................. 210/198.2; 210/502.1; 210/635; 210/656
[58] Field of Search ............... 210/635, 638, 643, 644, 210/656, 198.2, 321.72, 500.28, 500.38, 502.1; 556/400; 502/401, 402, 404

[56] References Cited

U.S. PATENT DOCUMENTS

| | | | |
|---|---|---|---|
| 4,322,310 | 3/1982 | House | 210/635 |
| 4,330,440 | 5/1982 | Ayers | 210/635 |
| 4,512,898 | 4/1985 | Oi | 210/656 |
| 4,565,877 | 1/1986 | Wada | 210/656 |
| 4,604,207 | 8/1986 | Oi | 210/656 |
| 4,627,919 | 12/1986 | Yuki | 198.2/ |
| 4,824,950 | 4/1989 | Barcza | 556/400 |
| 4,830,921 | 5/1989 | Kitayama | 210/198.2 |
| 4,909,935 | 3/1990 | Bradshaw et al. | 210/198.2 |
| 4,919,803 | 4/1990 | Doyle et al. | 210/198.2 |
| 4,963,254 | 10/1990 | Oi | 210/198.2 |
| 5,051,176 | 9/1991 | Miyano | 210/198.2 |
| 5,080,795 | 1/1992 | Pirkle | 210/643 |
| 5,149,426 | 9/1992 | Watabe | 210/198.2 |

FOREIGN PATENT DOCUMENTS 0299793 1/1989 European Pat. Off. ......... 210/198.2

OTHER PUBLICATIONS

Aoyama, et al. (1986) "Photocyclization of N,N-Dialkyl-$\beta$-$\gamma$-Unsaturated Amides. 1,6-Hydrogen Transfer Via Charge-Transfer States", J. Chem. Soc. Perkin Trans. 1, 1165–1169.

Pirkle, et al. (1992) "Effect of Superfluous Remote Polar Functionally on Chiral Recognition", Journal of Chromatography 589, 45–51.

Pirkle, et al. (1984) "A Rational Approach to the Design of Highly Effective Chiral Stationary Phases for the Liquid Chromatographic Separation of Enantiomers", Journal of Pharmaceutical & Biomedical Analysis 2, 173–181.

Pirkle, et al. (1984) "A Chiral Stationary Phase for the Facile Resolution of Amino Acids, Amino Alcohols
(List continued on next page.)

Primary Examiner—Ernest G. Therkorn
Attorney, Agent, or Firm—Scully, Scott, Murphy & Presser

[57] ABSTRACT

A high performance chiral selector having the formula:

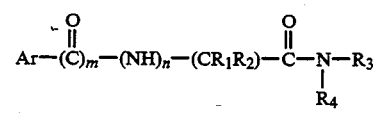

wherein
Ar is a monocyclic or ortho-fused polycyclic aromatic moiety having up to 10 ring carbon atoms, either of which may be unsubstituted or substituted with one or more $C_1$ to $C_6$ alkyl, $C_1$ to $C_6$ alkoxy, $NO_2$, $N(R_5)_3^+$, CN, $COOR_6$ $SO_3H$ and $COR_7$ groups wherein $R_5$, $R_6$ and $R_7$ are each independently hydrogen or $C_1$ to $C_6$ alkyl;

$R_1$ and $R_2$ are each independently hydrogen, $C_1$ to $C_6$ alkyl or phenyl;

$R_3$ and $R_4$ are each independently $C_1$ to $C_{12}$ alkyl or $C_2$ to $C_{12}$ alkenyl; and m and n are each independently zero or 1, said compound being an R or an S enantiomer or a mixture of R and S enantiomers.

12 Claims, 4 Drawing Sheets

NORMAL PHASE SEPARATION OF THE ENANTIOMERS OF LEUCINE 3,5 DIMETHYLANILIDE ALKYL CARBAMEATE SERIES ON CSP-1 AND CSP-2 CONDITIONS: FLOW RATE = 2.0 mL/min.; MOBILE PHASE = 5% 2-PROPANOL IN HEXANE. THE CHROMATOGRAPHIC SEPARATION FACTOR FOR THE ENANTIOMERS IS DESIGNATED α.

OTHER PUBLICATIONS and Amines as the N-3, 5-Dinitrobenzoyl Derivatives", The Journal of Organic Chemistry 49, 3043-3046.

Pirkle, et al. (1984) "A Rational Approach to the Design of Highly-Effective Chiral Stationary Phases", *Journal of Chromatography* 316, 585-604.

Pirkle, et al. (1985) "Preparation and Use of Hydantoin-Based Chiral Stationary Phases", *Journal of Chromatography* 322, 309-320.

Pirkle, et al. (1986) "Separation of the Enantiomers of 3,5-Dinitrophenyl Carbamates and 3,5-Dinitropenyl Ureas", *Journal of Liquid Chromatography* 9, 443-453.

Hyun, et al. (1987) "Preparation an Evaluation of a Chiral Stationary Phase Bearing Both π-Acidic and Basic Sites", *Journal of Chromatography* 393, 357-365.

Pirkle, et al. (1991) "Chromatographic Approach to the Measurement of the Interstrand Distance for Some Chiral Bonded Phases", *Anal. Chem.* 63, 16-20.

Pirkle, et al. (1991) "Chiral Stationary Phase Designed for β-Blockers", *Journal of Chromatography* 557, 173-185.

Pirkle, et al. (1989) "Separation of the Enantiomers of N-Protected α-Amino Acids as Anilide and 3,5-Dimethylanilide Derivatives", *Journal of Chromatography* 478, 419-423.

Pirkle, et al. (1985) "Effect of Interstrand Distance Upon Chiral Recognition By A Chiral Stationary Phase", *Journal of Chromatography* 328, 1-9.

Pirkle, et al. (1981) "Chiral High-Pressure Liquid Chromatographic Stationary Phases. 4. Separation of the Enantiomers of Bi-β-Napthols and Analogues", *J. Org. Chem.* 46, 4988-4991.

Wainer, et al. (1984) "Application of High-Performance Liquid Chromatographic Chiral Stationary Phases to Pharmaceutical Analysis: Structural and Conformation . . . Agents", *Journal of Chromatography* 284, 117-124.

Doyle, et al. (1985) "The Resolution of Enantiomeric Drugs Using HPLC Chiral Stationary Phases", *Pharmaceutical Technology*, 28, 30-32.

Wainer, et al. (1984) "The Application of HPLC Chiral Stationary Phases to Pharmaceutical Analysis: The Resolution of Some Tropic Acid Derivatives", *Journal of Liquid Chromatography* 7, 731-741.

Perry, et al., "Chiral Separations by HPLC. Theory and Practice: Developments With the Pirkle Covalent HPLC Column", No. 939 (undated), p. 1.

Wainer, et al. "Use of Chiral Stationary Phases to Resolve Molecules of Pharmacological Interest", *Liquid Chromatography* 2, 88-89, 97-98, 1984.

Bojarski (1989) "Chromatography of Enantiomers of 2-Arylpropionic Acids", *Journal of Liquid Chromatography* 12, 2685-2706.

Pirkle, et al. (1990) "The Separation of the Enantiomers of A Variety of Non-Steroidal Anti-Inflammatory Drugs (NSaids) As Their Anilide Derivatives Using A Chiral Stationary Phase", *Journal of Liquid Chromatography* 13, 2123-2134.

Pirkle, et al. (1989) "Improved Chiral Stationary Phase for the Separation of the Enantiomers of Chiral Acids as Their Anilide Derivatives", *Journal of Chromatography* 471, 271-281.

Pirkle, et al., (1989) "Use of Achiral Ion-Pairing Reagents with Chiral Stationary Phases", *Journal of Chromatography* 479, 377-386.

Pirkle, et al. (1991) "A Chiral Stationary Phase Which Affords Unusually High Levels of Enantioselectivity", *Chirality* 3, 183-187.

Pirkle, et al. (1988) "An Improved Chiral Stationary Phase for the Facile Separation of Enantiomers", *Journal of Chromatography* 441, 311-322.

Pirkle, et al. (1988) "Systematic Studies of Chiral Recognition Mechanisms", *Plenum Press*, 23-35.

Crossland, et al. (1970) "A Facile Synthesis of Methanesulfonate Esters", *J. Org. Chem.* 35, 3195-3196.

Pirkle, et al. (1986) "Intermolecular $^1H[^1H]$Nuclear Overhauser Effects in Diastereomeric Complexes: Support for a Chromatographically Derived Chiral Recognition Model", *J. Am. Chem. Soc.* 108, 5627-5628.

Pirkle, et al. (1987) "Reciprocity in Chiral Recognition Comparison of Several Chiral Stationary Phases", *Journal of Chromatography* 404, 107-115.

Pirkle, et al. (1987) "Section 5, Products for Chromatographic Chiral Separations, Regis Advance Pirkle-Concept Technology", *Regis*, 42-54.

A copy of the Search Report of PCT/US93/05933 dated Oct. 14, 1993 pp. 1-6.

An Abstract of Japan Patent No. 60-66162 dated Apr. 16, 1985.

FIGURE 1: NORMAL PHASE SEPARATION OF THE ENANTIOMERS OF LEUCINE 3,5 DIMETHYLANILIDE ALKYL CARBAMEATE SERIES ON CSP-1 AND CSP-2 CONDITIONS: FLOW RATE = 2.0 mL/min.; MOBILE PHASE = 5% 2-PROPANOL IN HEXANE. THE CHROMATOGRAPHIC SEPARATION FACTOR FOR THE ENANTIOMERS IS DESIGNATED $\alpha$.

FIGURE 2: REVERSE-PHASE SEPARATION OF THE ENANTIOMERS OF LEUCINE 3,5 DIMETHYLANILIDE ALKYL CARBAMEATE SERIES ON CSP-1 AND CSP-2. CONDITIONS: FLOW RATE = 2.0 mL/min.; MOBILE PHASE = 80% METHANOL/WATER. THE CHROMATOGRAPHIC SEPARATION FACTOR FOR THE ENANTIOMERS IS DESIGNATED $\alpha$.

FIGURE 3: NORMAL PHASE SEPARATION OF THE ENANTIOMERS OF LEUCINE 3,5-DIMETHYLANILIDE ALKYL CARBAMEATE SERIES ON CSP 3, 4,5,6 AND 7. CONDITIONS: FLOW RATE = 2.0 mL/min.; MOBILE PHASE = 5% 2-PROPANOL IN HEXANE. THE CHROMATOGRAPHIC SEPARATION FACTOR FOR THE ENANTIOMERS IS DESIGNATED $\alpha$.

FIGURE 4: REVERSE-PHASE SEPARATION OF THE ENANTIOMERS OF LEUCINE 3,5-DIMETHYLANILIDE ALKYL CARBAMEATE SERIES ON CSP's 3,4,5,6 AND 7. CONDITIONS: FLOW RATE = 2.0 mL/min.; MOBILE PHASE = 80% METHANOL/WATER. THE CHROMATOGRAPHIC SEPARATION FACTOR FOR THE ENANTIOMERS IS DESIGNATED $\alpha$.

HIGH PERFORMANCE CHIRAL SELECTOR

This invention was made with Government support under Grant No. CHE-8714950 awarded by the National Science Foundation. The Government has certain rights in the invention.

This is a divisional of application Ser. No. 902,616, filed on Jun. 23, 1992, now U.S. Pat. No. 5,290,440.

BACKGROUND OF THE INVENTION

1. Field of the Invention

The present invention relates to the separation of enantiomers, i.e., those isomers in which the arrangement of atoms or groups is such that the two molecules are not superimposable. The invention more particularly relates to a high performance chiral selector useful, for example, as a chiral stationary phase (CSP) in liquid chromatographic separation of enantiomers.

2. Description of the Prior Art

Stereoisomers are those molecules which differ from each other only in the way their atoms are oriented in space. Stereoisomers are generally classified as diastereomers or enantiomers; the latter embracing those which are mirror-images of each other, the former being those which are not. The particular arrangement of atoms that characterize a particular stereoisomer is known as its optical configuration, specified by known sequencing rules as, for example, either + or − (also D or L) and/or R or S.

Though differing only in orientation, the practical effects of stereoisomerism are important. For example, the biological and pharmaceutical activities of many compounds are strongly influenced by the particular configuration involved. Indeed, many compounds are only of widespread utility when employed in a given stereoisomeric form.

Living organisms usually produce only one enantiomer of a pair. Thus only (−)-2-methyl-1-butanol is formed in yeast fermentation of starches; only (+)-lactic acid is formed in the contraction of muscle; fruit juices contain only (−)-malic acid, and only (−)-quinine is obtained from the cinchona tree. In biological systems, stereochemical specificity is the rule rather than the exception, since the catalytic enzymes, which are so important in such systems, are optically active. For example, the sugar (+)-glucose plays an important role in animal metabolism and is the basic raw material in the fermentation industry; however, its optical counterpart, or antipode, (−)-glucose, is neither metabolized by animals nor fermented by yeasts. Other examples in this regard include the mold *Penicillium glaucum*, which will only consume the (+)-enantiomer of the enantiomeric mixture of tartaric acid, leaving the (−)-enantiomer intact. Also, only one stereoisomer of chloromycetin is an antibiotic; and (+)-ephedrine not only does not have any drug activity, but it interferes with the drug activity of its antipode. Finally, in the world of essences, the enantiomer (−)-carvone provides oil of spearmint with its distinctive odor, while its optical counterpart (+)-carvone provides the essence of caraway.

Accordingly, it is desirable and oftentimes essential to separate stereoisomers in order to obtain the useful version of a compound that is optically active.

Separation in this regard is generally not a problem when diastereomers are involved: diastereomers have different physical properties, such as melting points, boiling points, solubilities in a given solvent, densities, refractive indices etc. Hence, diastereomers are normally separated from one another by conventional methods, such as fractional distillation, fractional crystallization or chromatography.

Enantiomers, on the other hand, present a special problem because their physical properties are identical. Thus they cannot as a rule—and especially so when in the form of a racemic mixture—be separated by ordinary methods: not by fractional distillation, because their boiling points are identical; not by conventional crystallization because (unless the solvent is optically active) their solubilities are identical; not by conventional chromatography because (unless the adsorbent is optically active) they are held equally onto the adsorbent. The problem of separating enantiomers is further exacerbated by the fact that conventional synthetic techniques almost always produce a mixture of enantiomers. When a mixture comprises equal amounts of enantiomers having opposite optical configurations, it is called a racemate; separation of a racemate into its respective enantiomers is generally known as a resolution, and is a process of considerable importance.

Various techniques for separating enantiomers are known. Most, however, are directed to small, analytical quantities, meaning that other drawbacks aside, when applied to preparative scale amounts (the milligram to kilogram range) a loss of resolution occurs. Hand separation, the oldest method of resolution, is not only impractical but can almost never be used since racemates seldom form mixtures of crystals recognizable as mirror images.

Another method, known as indirect separation, involves the conversion of a mixture of enantiomers—the racemate—into a mixture of diastereomers. The conversion is accomplished by reacting the enantiomers with an optically pure derivatizing agent. The resultant diastereomers are then separated from one another by taking advantage of their different physical properties. Once separated by, for example, fractional crystallization, or more commonly, chromatography, the diastereomers are re-converted back into the corresponding enantiomers, which are now optically pure. Though achieving the requisite separation, the indirect method suffers in that it is time consuming and can require large quantities of optically pure derivatizing agent which can be expensive and is oftentimes not recoverable. Moreover, the de-derivatizing step may itself result in racemization thus defeating the purpose of the separation earlier achieved.

A more current method that avoids some of the drawbacks attendant the indirect method is known as the direct method of separation. The direct method, much like the indirect method, involves the formation of a diastereomeric species. However, unlike the indirect method, this species is transient, with the stability of one species differing from the other.

In one application of the direct method, as disclosed, e.g., in copending and commonly assigned U.S. patent application Ser. No. 528,007, filed May 23, 1990, now U.S. Pat. No. 5,080,795 the contents of which are incorporated herein by reference, enantiomers of compounds such as amino acids, amino esters, alcohols, amines, sulfonic acid or derivatives thereof are separated by means of a liquid membrane that contains a chiral carrier, such as the derivatized amino acid (S)-N-(1-naphthyl)leucine octadecyl ester. The chiral carrier is capable of forming a stable complex with one of the enantiomeric configurations. The liquid membrane is located on one side of a semi-permeable barrier and the mixture of enantiomers is located on the other side of the barrier. The liquid membrane containing the chiral carrier impregnates the semi-permeable barrier under conditions effective to permit or cause a stable complex between the chiral carrier and one of the enantiomeric configurations to form in the barrier. The liquid membrane containing the stable complex is passed to a second location where the conditions are effective to dissociate the stable complex, thus allowing the recovery of the complex-forming enantiomer to take place. In one embodiment of this application, a hollow membrane fiber membrane is employed as the semi-permeable barrier.

In another, more common application of the direct method, the mixture of enantiomers is allowed to interact with a chiral stationary phase as resides, e.g., in a chromatographic column. The enantiomer that interacts more strongly with the chiral stationary phase will have a longer residence time in the column; hence, a separation of enantiomers will occur. Further, when the mode of interaction with the chiral stationary phase can be characterized, the elution order can be predicted.

Examples of chiral stationary phases include those based upon (L)-N-(3,5-dinitrobenzoyl)leucine, which is useful in separating enantiomers of N-aryl derivatized amino acids and esters, and those based upon (L)-N-(1-naphthyl)leucine which has been effectively used to separate N-(3,5-dinitrobenzoyl) derivatized amino compounds. High performance liquid chromatographic (HPLC) columns packed with silica-bonded CSP's of a variety of K-electron acceptors and $\pi$-electron donors—including derivatives of phenylglycine, leucine, naphthylalanine and naphthylleucine are commercially available from Regis Chemical Company, Morton Grove, Ill.

Other examples of chiral stationary phases used in the direct separation of enantiomers include, e.g., that based upon N-(3,5-dinitrobenzoyl)-$\alpha$-amino-2,2-dimethyl-4-pentenyl phosphonate, as particularly described in commonly assigned U.S. patent application Ser. No. 761,212, filed on Sep. 17,1991, now U.S. Pat. No. 5,254,248, which is useful in separating enantiomers of $\beta$-amino alcohol compounds, such as $\beta$-blockers; and that based upon 4-(3,5-dinitrobenzoyl)amino-3-(undec-10-enyl)-1,2,3,4-tetrahydrophrenanthrene, as particular described in commonly assigned U.S. patent application Ser. No. 763,043, filed Sep. 20, 1991, now abandoned, which is useful in separating enantiomers of non-steroidal anti-inflammatory agents, such as naproxen.

While these efforts indicate that there is a wide variety of useful chiral selectors available, there nevertheless continues to be a pressing need for chiral selectors having analytical and, importantly, preparative scale applicability over a broad range of enantiomeric compounds, especially chiral selectors that evince decreased retention and increased selectivity so as to provide improved qualitative separations of these compounds.

SUMMARY OF THE INVENTION

The present invention is directed to a high performance chiral selector that represents an improvement in the art of enantiomeric separation. The chiral selector of the present invention is designed to eliminate adsorption sites that are superfluous to the chiral recognition process, thus affording increased enantioselectivity and when employed in a liquid chromatographic column, decreased retention.

The chiral selector of the present invention is a compound having the formula:

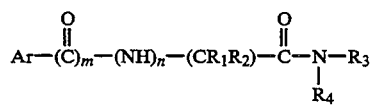

wherein

Ar is a monocyclic or ortho-fused polycyclic aromatic moiety having up to 10 ring carbon atoms, either of which may be unsubstituted or substituted with one or more $C_1$ to $C_6$ alkyl, $C_1$ to $C_6$ alkoxy, nitro ($NO_2$), $N(R_5)_3^+$, CN, $COOR_6$, $SO_3H$ and $COR_7$ groups wherein $R_5$, $R_6$ and $R_7$ are each independently hydrogen or $C_1$ to $C_6$ alkyl;

$R_1$ and $R_2$ are each independently hydrogen, $C_1$ to $C_6$ alkyl or phenyl;

$R_3$ and $R_4$ are each independently $C_1$ to $C_{12}$ alkyl or $C_2$ to $C_{12}$ alkenyl; and m and n are each independently 0 or 1, said compound being an R or an S enantiomer or a mixture of R and S enantiomers.

In one embodiment of the subject invention, the chiral selector is employed in a process of separating enantiomers of compounds wherein said compounds have first and second optical configuration, which comprises contacting a mixture of said enantiomers with the chiral selector described above, said selector being an R or S enantiomer, under conditions effective to form a complex between an enantiomer of said compound having said first optical configuration and said chiral selector, and recovering the non-complexed enantiomer of said compound having said second optical configuration. Examples of compounds whose enantiomers may be separated by the process of the present invention include alkyl carbameate derivatives of leucine 3,5-dimethylanilide; amides of 3,5-dinitrobenzoyl leucine; arylacetic acid compounds, including naproxen; $\beta$-amino alcohol compounds, including those known as $\beta$-blockers; and dinitrobenzoyl derivatives of various simple amines or $\alpha$-amino esters, among other compounds to which the present invention has applicability.

The present invention is also directed to an apparatus employing the chiral selector for purposes of enantiomeric separation or recognition. Apparatuses in this regard include, e.g., liquid chromatographic columns, such as high performance liquid chromatographic (HPLC) columns, enantioselective membrane transport devices and liquid-liquid partitionum equipment, such as countercurrent chromatographic devices.

DETAILED DESCRIPTION OF THE INVENTION

Figure 1:
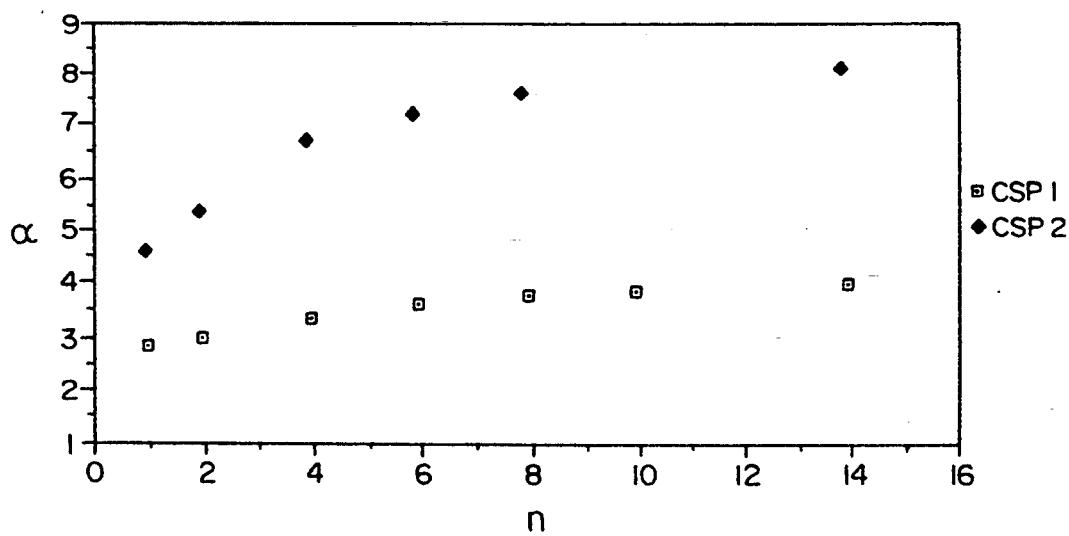
FIG. 1 is a graph showing the normal phase separation of the enantiomers of a series of alkyl carbameate derivatives of leucine 3,5-dimethylanilide using a preferred chiral selector of the present invention as compared to a commercially available chiral selector.

The present invention relates to a high performance chiral selector that exhibits improved enantioselectivity over a broad spectrum of enantiomeric compounds.

In one aspect of the invention, the instant chiral selector is designed to eliminate adsorption sites that are either non-essential to the chiral recognition process or that are detrimental to the same. For example, in chromatographic applications known heretofore, a chiral selector is tethered to a support such as silica by means of an amide linkage that is derived from a primary amine. The resultant amide hydrogen in the connecting tether has now been found to be a potential interaction site which, under normal circumstances, plays no significant role in the chiral recognition process; it does, however, contribute to overall retention.

The chiral selector of the invention eliminates the presence of an amide hydrogen in the first instance, and thus eliminates the potential for any superfluous interaction caused by such a hydrogen. The chiral selector of the invention provides an amide linkage to a secondary, rather than a primary amine. By replacing the amide hydrogen with, e.g., an alkyl group, to thus generate a secondary amine the chiral selector of the invention, and chiral stationary phases (CSP's) made therefrom, generally show decreased retention and increased enantioselectivity in the separation of enantiomers.

The chiral selector of the invention is a compound having the formula:

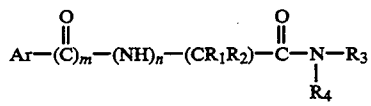

wherein
Ar is a monocyclic or ortho-fused polycyclic aromatic moiety having up to 10 ring carbon atoms, either of which may be unsubstituted or substituted with one or more $C_1$ to $C_6$ alkyl, $C_1$ to $C_6$ alkoxy, nitro ($NO_2$), $N(R_5)_3^+$, CN, $COOR_6$, $SO_3H$ and $COR_7$ groups wherein $R_5$, $R_6$ and $R_7$ are each independently hydrogen or $C_1$ to $C_6$ alkyl.

A preferred monocyclic aromatic moiety is phenyl; preferred ortho-fused polycyclic aromatic moieties include α-naphthyl and β-naphthyl. Preferred substituents, when present, include one or more of $C_1$ to $C_6$ alkyl, preferably methyl; $C_1$ to $C_6$ alkoxy, preferably methoxy; and $NO_2$.

As employed herein, the $C_1$ to $C_6$ alkyl groups may be in the normal or branched configuration and include, e.g., methyl, ethyl, propyl, isopropyl, butyl, isobutyl, t-butyl, amyl, pentyl, hexyl and the like. The preferred $C_1$ to $C_6$ alkyl is $C_1$ to $C_3$; most preferred is methyl, As employed herein, the $C_1$ to $C_6$ alkoxy groups may be in the normal or branched configuration and include, e.g., methoxy, ethoxy, propoxy, butoxy, pentoxy, hexoxy and the like. The preferred $C_1$ to $C_6$ alkoxy has 3 carbon atoms. The most preferred alkoxy is methoxy.

Examples of preferred substituted aromatic moieties include 3,5-dinitrophenyl, 6-methoxy-3-naphthyl and 6,7-dimethyl-α-naphthyl.

In the chiral selector having the formula described above, $R_1$ and $R_2$ are each independently hydrogen, $C_1$ to $C_6$ alkyl, aryl, aralkyl or alkaryl.

As employed herein, the aryl groups are aromatic rings containing 6 to 10 ring carbon atoms. Preferred aryl groups include monocyclic or ortho-fused polycyclic aromatics, such as phenyl, α-naphthyl and β-naphthyl.

The aralkyl groups contain up to 16 carbon atoms with each aryl group containing from 6 to 10 carbon atoms, and each alkyl group containing up to 6 carbon atoms which may be in the branched or normal configuration. Preferably, each aryl group contains up to 6 carbon atoms and each alkyl group contains 1 to 3 carbon atoms. A particularly preferred aralkyl in benzyl.

The alkaryl groups contain up to 16 carbon atoms with each alkyl group containing up to 6 carbon atoms which may be in the normal or branched configuration, and each aryl group containing from 6 to 10 carbon atoms. Preferably, each alkyl group contains 1 to 3 carbon atoms and each aryl group contains up to 6 carbon atoms. A particularly preferred alkaryl is tolyl.

In preferred embodiments, $R_1$ is hydrogen and $R_2$ is $C_1$ to $C_6$ alkyl or aryl. Examples of particularly preferred $C_1$ to $C_6$ alkyls in this embodiment include methyl and isobutyl. A particularly preferred aryl in this embodiment is phenyl.

$R_3$ and $R_4$ are each independently $C_1$ to $C_{12}$ alkyl or $C_2$ to $C_{12}$ alkenyl. The $C_1$ to $C_{12}$ alkyl groups may be in the normal or branched configuration and include, e.g., methyl, ethyl, propyl, isopropyl, butyl, isobutyl, t-butyl, amyl, pentyl, hexyl, heptyl, octyl, nonyl, decyl, undecyl and the like. The $C_2$ to $C_{12}$ alkenyl groups may be in the normal or branched configuration. Preferable $C_2$ to $C_{12}$ alkenyls include ethenyl, 2-propenyl, 3-butenyl, 4-pentenyl, 5-hexenyl, 6-heptenyl, 7-octenyl, 8-nonenyl, 9-decenyl and 10-undecenyl.

The subscripts m and n in the formula defined above are each independently 0 or 1; preferably, m and n are each 1 when Ar is a monocyclic aromatic moiety, and m is 0 when Ar is a ortho-fused polycyclic aromatic moiety.

In a first embodiment of the present invention, Ar is phenyl substituted with one or more $NO_2$ groups, $R_{12}$ is hydrogen and m and n are each 1. In one aspect of this first embodiment $R_3$ and $R_4$ are each independently $C_1$ to $C_3$ alkyl or $C_2$ to $C_6$ alkenyl. In a preferred configuration of this aspect of the first embodiment, denoted hereinafter as CS-4, Ar is 3,5-dinitrophenyl, $R_2$ is isobutyl, $R_3$ is 2-propenyl and $R_4$ is methyl. The structure of CS-4 is shown below:

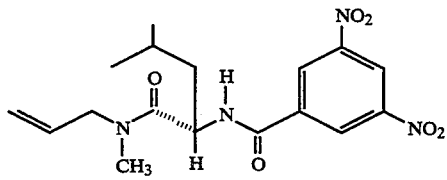

In a second preferred configuration of this one aspect, denoted hereinafter as CS-4A, Ar is 3,5-dinitrophenyl, $R_2$ is phenyl, $R_3$ is 2-propenyl and $R_4$ is methyl. The structure of CS-4A is shown below, with phenyl denoted as Ph.

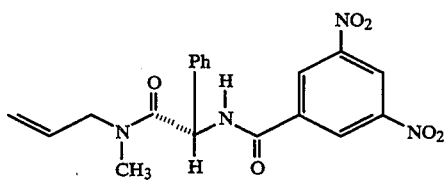

In a second embodiment of the present invention, Ar is unsubstituted α-naphthyl or β-naphthyl, $R_1$ is hydrogen, m is 0 and n is 1. In one aspect of this second embodiment, $R_3$ is $C_2$ to $C_{12}$ alkenyl and $R_4$ is $C_1$ to $C_3$ alkyl. In a preferred configuration of this aspect of the second embodiment, denoted hereinafter as CS-9, Ar is unsubstituted 5-naphthyl, $R_2$ is methyl, $R_3$ is 10-undecenyl and $R_4$ is methyl. The structure of CS-9 is shown below.

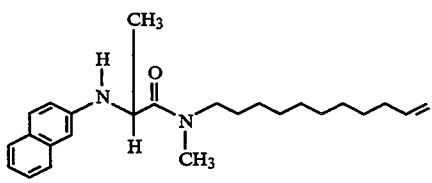

In a second preferred configuration of this aspect of the second embodiment, denoted hereinafter as CS-9A, Ar is unsubstituted β-naphthyl, $R_2$ is isobutyl, $R_3$ is 10-undecenyl and $R_4$ is methyl. The structure of, CS-9A is shown below.

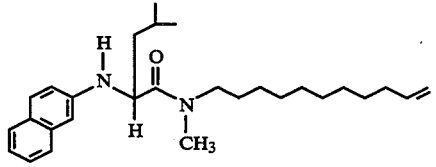

In a third embodiment of the present invention, Ar is α-naphthyl or β-naphthyl substituted with one or more lower alkoxy groups, $R_1$ is hydrogen, and m and n are each 0. In one aspect of this third embodiment, $R_3$ is $C_2$ to $C_{12}$ alkenyl and $R_4$ is $C_1$ to $C_9$ alkyl. In a preferred configuration of this aspect of the third embodiment, denoted hereinafter as CS-11, Ar is 7-methoxy-3-naphthyl, $R_2$ is methyl, $R_3$ is 2-propenyl and $R_4$ is methyl. The structure of CS-11 is shown below.

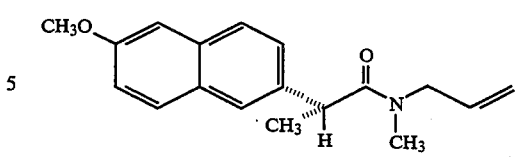

In a second preferred configuration of this aspect of the third embodiment, denoted hereinafter as CS-12, Ar is a 7-methoxy-3-naphthyl, $R_2$ is methyl, $R_3$ is 10-undecenyl, and $R_4$ is n-octyl. The structure of CS-12 is shown below.

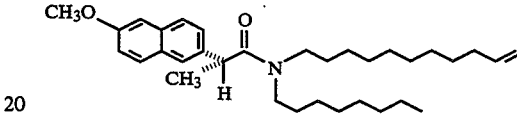

In a fourth embodiment of the present invention, Ar is phenyl substituted with one or more $NO_2$ groups, $R_2$ is hydrogen and m and n are each 1. In one aspect of this fourth embodiment, denoted hereinafter as CS-7, Ar is 3,5-dinitrophenyl, $R_2$ is isobutyl and $R_2$ and $R_4$ are each 2-propenyl. The structure of CS-7 is shown below.

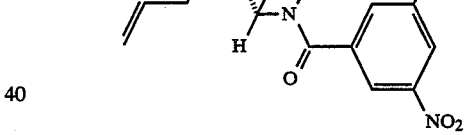

In a second aspect of this fourth embodiment, denoted hereinafter as CS-7A, Ar is 3,5-dinitrophenyl, $R_2$ is phenyl and $R_3$ and $R_4$ are each propenyl. The structure of CS-7A is shown below.

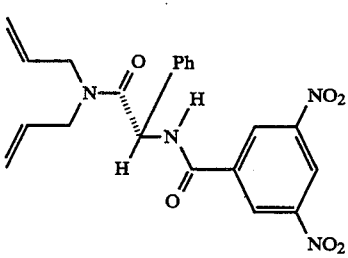

In a fifth embodiment of the present invention, Ar is unsubstituted α-naphthyl or B-naphthyl, $R_1$ is hydrogen, m is 0 and n is 1. In one aspect of this fifth embodiment, $R_3$ and $R_4$ are each $C_2$ to $C_6$ alkenyl. In a preferred configuration of this aspect of the fifth embodiment, denoted hereinafter as CS-7B, Ar is unsubstituted α-naphthyl, $R_2$ is methyl and $R_3$ and $R_4$ are each 2-propenyl. The structure of CS-7B is shown below.

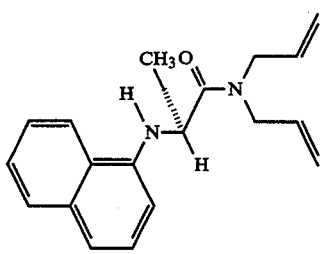

CS-7B

In a second preferred configuration of the fifth embodiment, denoted hereinafter as CS-7C, Ar is unsubstituted α-naphthyl, $R_2$ is isobutyl and $R_3$ and $R_4$ are each 2-propenyl. The structure of CS-7C is shown below.

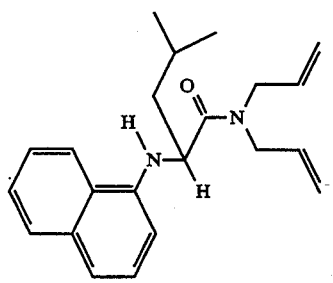

CS-7C

In a sixth embodiment of the present invention, Ar is phenyl substituted with one or more $NO_2$ groups, $R_1$ is hydrogen and m and n are each 1. In one aspect of this sixth embodiment $R_3$ is $C_7$ to $C_{12}$ alkenyl and $R_4$ is $C_1$ to $C_3$ alkyl. In a preferred configuration of this aspect of the sixth embodiment, denoted hereinafter as CS-6, Ar is 3,5-dinitrophenyl, $R_2$ is isobutyl, $R_3$ is 10-undecenyl and $R_4$ is methyl. The structure of CS-6 is shown below.

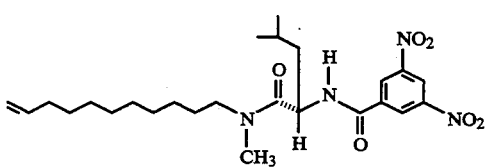

CS-6

The chiral selectors of the present invention that are embodied above may be prepared by conventional chemical preparative techniques, as will be exemplified for CS-4, CS-6, CS-7, CS-9 and CS-11. One of skill in the art will readily appreciate the modifications necessary to prepare other chiral selectors within the scope of the chemical formula employed herein.

Enantiomeric separation using the chiral selector of the invention may be achieved in a variety of techniques known in the art. In one embodiment in this regard, the chiral selector may form the active portion of the stationary phase in an HPLC column using techniques known in the art, such as hydrosilation followed by immobilization on a support effective for use in chromatographic separation. Supports useful in this regard include, e.g., silica and alumina.

Since the chiral selector of the invention is optically active, it is necessary to separate the chiral selector so that either the R or the S enantiomer of the chiral selector is employed as part of the stationary phase in the column, the choice depending upon which of the enantiomers to be separated is to be preferentially bound to the chiral selector. In this embodiment, $R_3$ must be alkenyl so as to permit the chiral selector to be immobilized on a support which is suitable for use in chromatographic applications. In one configuration, the chiral selector is immobilized by covalently bonding it to silanized silica.

Although a stationary phase formed using the chiral selector of the present invention may be prepared from multifunctional, e.g., trifunctional, silane precursors, it is preferred that the stationary phase be prepared using monofunctional silane precursors. The preference for using monofunctional silane precursors is because stationary phases derived from multifunctional silanes are, at least theoretically, more heterogenous than those derived from multifunctional silanes. This increased heterogeneous character is manifested by the fact that the bonding of a multifunctional silane, such as a trifunctional silane, to the silica surface can occur through one, two or three Si-O-Si linkages; additionally, polymerization of multifunctional silanes at the silica gel surface may occur. In contrast, a monofunctional silane can be bound to silica in only one manner; further, they are less reactive and can be easily purified chromatographically and readily characterized.

Thus in one aspect, the present invention relates to the utilization of the chiral selector of the invention in an HPLC stationary phase where said chiral selector is linked to the support material, such as silica, through either a multifunctional or a monofunctional linkage, the monofunctional linkage is preferred. In another aspect, the present invention relates to an improvement to chromatographic columns of the type known heretofore; the improvement comprising the use of a monofunctional silane linkage to connect the active portions of the stationary phases employed in these columns, to a support material such as silica. A particular class of chromatographic columns to which this improvement especially relates are those of the type containing a derivative of a 3,5-dinitrobenzoyl amino acid or a derivative of a naphthyl amino acid. Examples of columns in this type that are those commercially available from Regis Chemical Company, Morton Grove, Ill., and include columns whose stationary phases incorporate as an active part, 3,5-dinitrobenzoyl leucine; 3,5-dinitrobenzoyl phenylglycine; naphthylalanine; and naphthylleucine.

The monofunctional linkage contemplated by the present invention, with silica (denoted herein as $SiO_2$) as the support, has the formula:

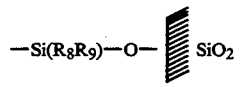

wherein $R_8$ and $R_($ are each independently hydrogen or $C_1$ to $C_6$ alkyl, preferably methyl. Thus in the practice of the present invention, when $R_3$ is alkenyl and $R_4$ is alkyl or hydrogen, the terminal end of $R_3$, whereat the double bond is preferably located when $R_3$ is alkenyl, attaches to the silicon of the above formula; when $R_3$ and $R_4$ are both alkenyl, than the monofunctional silane linkage contemplated by the invention has the formula:

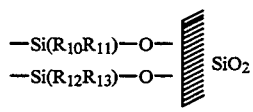

wherein $R_{10}$, $R_{11}$, $R_{12}$ and $R_{13}$ are each independently hydrogen or $C_1$ to $C_6$ alkyl; preferably methyl. In this embodiment, the terminal ends of $R_3$ and $R_4$, whereat the double bonds are preferably located, will attach to the respective silicons of the above formula.

In another embodiment, the chiral selector of the invention may be utilized to effect separations employing semi-permeable membranes wherein the chiral selector forms part of a mobile phase. Such techniques include the use of semi-permeable membranes that are in the form of hollow fiber membranes. In this embodiment of the invention, it is preferred that $R_3$ and $R_4$ are alkyl, preferably a $C_1$ to $C_6$ alkyl. This is because it is preferable that the terminal ends of $R_3$ and $R_4$ are each hydrogen so to minimize covalent bonding by the chiral selector. In one particularly useful embodiment in this regard, the chiral selector forms part of a liquid membrane passing on one side of a semi-permeable barrier with the enantiomers to be separated passing on the other side of the barrier. The pores of the barrier become impregnated with the liquid membrane containing the chiral selector. One of the enantiomers complexes with the chiral selector, passes through the barrier into the moving liquid membrane and is conducted to a second location where disassociation takes place. This technique is generally disclosed in commonly assigned U.S. patent application Ser. No. 528,007, filed May 23, 1990, now U.S. Pat. No. 5,080,795 the contents of which are incorporated herein by reference.

The following examples are given to illustrate the scope of the invention. These examples are given for illustrative purposes only, and the scope of the present invention should not be limited thereto.

EXAMPLES

A series of experiments was conducted to examine the performance of stationary phases formed in accordance with the present invention. Specifically, the chiral stationary bases formed in this regard utilized the chiral selector of the present invention wherein non-specific adsorption sites were eliminated. Multifunctional linkages to silica, as well as monofunctional linkages prepared in accordance with the present invention, were also evaluated in these experiments.

The chiral stationary phases that were evaluated in these experiments are shown in Table 1, below. As used herein, "Et" denotes "—$C_2H_5$" "Me" denotes "—$CH_3$".

TABLE 1
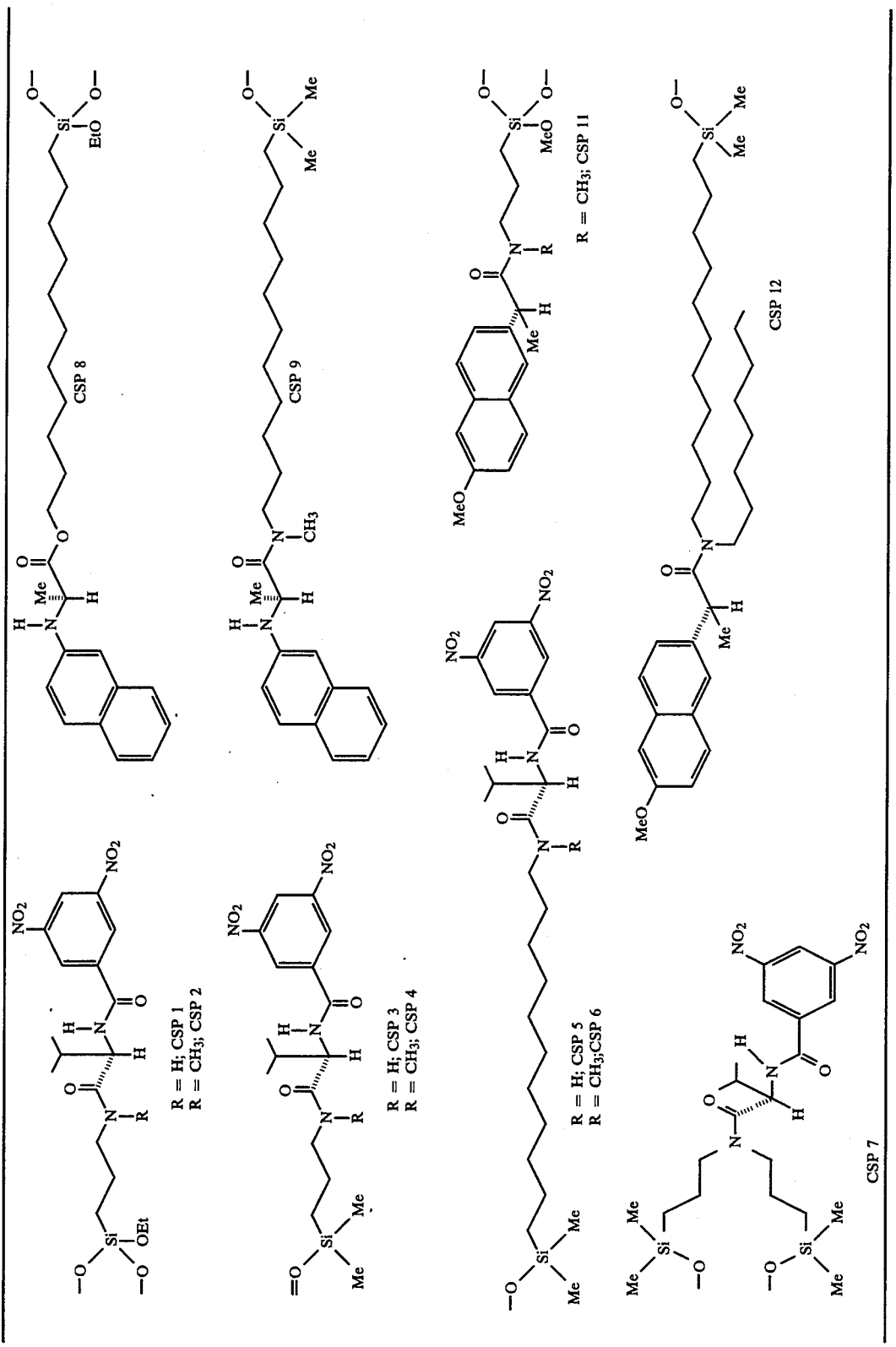

Of the chiral stationary phases shown in Table 1, CSP-2, CSP-4, CSP-6, CSP-7, CSP-9, CSP-11 and CSP-12 were formed utilizing various embodiments of the chiral selector of the present invention. CSP-2 and CSP-11 were secured to a silica support using a conventional multifunctional linkage. CSP-4, CSP-6, CSP-9 and CSP-12 were secured to a silica support using a monofunctional linkage as contemplated by the present invention; CSP-7 was secured by both arms, $R_3$ and $R_4$ to a silica support using a monofunctional linkage in accordance with the present invention. CSP-3 was formed using a known chiral selector as an active portion; CSP-3 was, however, secured to a silica support using a monofunctional linkage of the type contemplated by the invention.

CSP-1, CSP-5 and CSP-8 were chiral stationary phases conventionally known and commercially available from Regis Chemical Company, Morton Grove, Ill.

MATERIALS AND APPARATUS

In all of the following examples, the reagents used were of pharmaceutical or reagent grade and were used without further purification. Solvents used were HPLC grade or were distilled prior to use. Chromatographic analysis was performed using an Altex Model 100A pump, a Rheodyne Model 7125 injector with a 20 μL sample loop, a Linear UVIS 200 variable wavelength absorbance monitor, set at 254 nm, and a Hewlett-Packard HP 3394A integrating recorder. All chromatographic experiments were carried out at a nominal flow rate of 2.00 mL/min. unless otherwise indicated. In the normal phase mode, column void time was measured by injection of tri-t-butyl benzene, a presumed unretained solute, as described by Pirkle, et al. in *J. Liq. Chromatogr.*, 14, 1, 1991, the contents of which are incorporated herein by reference. Solvents used were HPLC grade or were distilled prior to use. All $^1H$ NMR spectra were recorded on a Varian XL 200 FT NMR spectrometer. $^1H$ NMR chemical shifts are reported in ppm relative to tetramethylsilane. Dimethylchlorosilane, 3-aminopropyltriethoxysilane, and N-methyl-3-aminopropyltriethoxysilane, were obtained from Petrarch Systems, Inc., Bristol, Pa. CSP-8 and Rexchrom 5μ, 100 Å A silica gel were obtained from Regis Chemical Company, Morton Grove, Ill.

PREPARATION OF CSP-1

The synthetic route for the preparation of CSP-1, which may also be commercially obtained from Regis Chemical Corporation, Morton Grove, Ill. is shown in Table 2, below.

TABLE 2

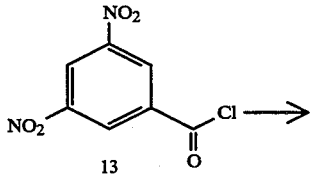

-continued
TABLE 2

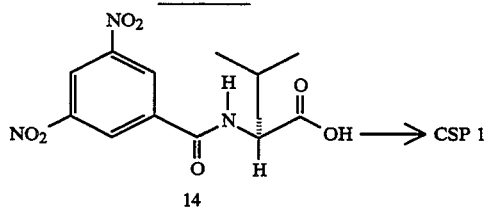

Synthetic Route for Preparation of CSP-1.

Preparation of 3,5-dinitrobenzoyl-(S)-leucine, (Table 2, Compound 14):

(S)-Leucine (10 g) was suspended in 150 mL dry tetrahydrofuran and chilled in an ice bath while stirring under a nitrogen atmosphere. 3,5-Dinitrobenzoyl chloride (Table 2, Compound 13, 21 g) and propylene oxide (6.6 g) were added; the resulting heterogeneous mixture became clear after several minutes. The mixture was allowed to stir for 5 h, and was evaporated under reduced pressure to afford an oil which crystallized upon addition of 100 mL of cold dichloromethane. Filtration and drying of the resulting crystals afforded 3,5-dinitrobenzoyl-(S)-leucine, 14, as a white solid (20.64 g, 83% yield). $^1H$ NMR (200 MHz, $d_6$DMSO) δ: 0.95 (m,6H), 1.75 (M,3H), 4.25 (m,1H), 9.00 (t,1H), 9.17 (d,2H), 9.41 (d,1H).

Preparation of 3-aminopropyl Silica:

Silica gel (5.0 g, Regis Rexchrom 5μ/100 Å) was placed in a 100 mL round bottom flask fitted with a boiling stick, Dean-Stark trap, and condenser. Benzene (50 mL) was added, and the mixture was heated at reflux for several hours. Dimethylformamide (1 mL) was then added to the benzene slurry, and the sample was evaporated to near dryness on a rotary evaporator. A dichloromethane solution of 3-aminopropyltriethoxysilane (1.0 g) was then added, and the resulting slurry was sonicated for several minutes, then evaporated to near dryness. The sample was again slurried in dichloromethane, sonicated, and evaporated to near dryness; this sequence was repeated several times to insure complete coverage of the silica gel.

The nearly dry silica gel-silane mixture was then heated with rocking on a Kügelrohr distillation apparatus (120° C., 1 torr, 18 h). The silica gel was then slurried in ethanol, filtered through a fine sintered glass funnel, and washed repeatedly with methanol. The washed silica gel was then slurried in methanol and packed into a 4.6 mm I.D.×25 cm length stainless steel HPLC column using an air driven Haskell pump operating at about 9000 psi. Recovered excess stationary phase from the column packer was dried thoroughly under high vacuum; elemental analysis indicated a loading of $4.0 \times 10^{-4}$ moles of aminopropyl groups per gram of stationary phase.

Preparation of the Stationary Phase, CSP-1:

Acid, 14, (2.0 g) was suspended in 100 mL of dry tetrahydrofuran and stirred at 0° C. 1-ethoxycarbonyl-2-ethoxy-1-quinolinecarboxylate (EEDQ, 2.0 g) was added, and the resulting mixture was stirred for 45 min. The mixture of activated acid thus obtained was pumped through a column containing the 3-aminopropyl silica, as prepared above, which had been equilibrated with tetrahydrofuran. The column was then sequentially eluted with methanol and then 20% 2-propanol in hexane.

PREPARATION OF CSP-2

CSP-2, which contained a methyl group in place of the amide hydrogen of CSP-1, was formed using as an active portion, a chiral selector of the present invention. The active portion was secured to silica via a conventional multifunctional linkage. The synthetic route for the preparation of CSP-2 in this regard is shown in Table 3, below.

TABLE 3

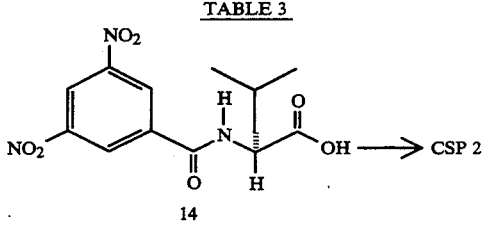

14

Synthetic Route for Preparation of CSP-2

Preparation of N methyl 3-aminopropyl silica:

The preparation of N-methyl-3-aminopropyl silica followed the procedure reported for the preparation of 3-aminopropyl silica in CSP-1 Supra except that N-methyl 3-aminopropyltriethoxysilane was used. Combustion analysis of residual silica removed from the column packer revealed a loading of $4.0 \times 10^{-4}$ moles of aminosilane per gram of stationary phase.

Preparation of the Stationary Phase, CSP-2:

Preparation of the stationary phase, CSP-2, followed the procedure for the preparation of the stationary phase step in the preparation of CSP-1, supra.

PREPARATION OF CSP-3

CSP-3 contained the commercially available chiral selector portion of CSP-1; however, CSP-3 was immobilized to silica by way of a monofunctional linkage in accordance with the present invention. The synthetic route for the preparation of CSP-3, the monofunctional silane analog of CSP-1 is shown in Table 4, below.

TABLE 4

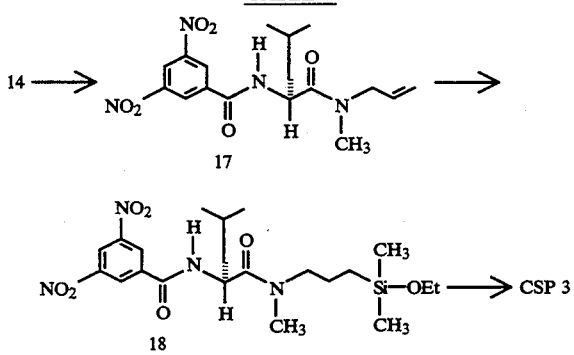

Synthetic route for preparation of CSP-3

Preparation of the Allylamide (Table 4, Compound 17):

3,5-dinitrobenzoyl-(S)-leucine, prepared as described in the procedure for CSP-1 Supra, (5.0 g) was suspended in 100 mL of dry tetrahydrofuran and stirred at 0° C. 1-Ethoxycarbonyl-2-ethoxy-1-quinolinecarboxylate (EEDQ, 3.8 g) was added, and the resulting mixture was stirred for 45 min. Allylamine (0.88 g) was then added slowly via syringe, and the resulting solution was allowed to gradually warm to room temperature while stirring under a nitrogen atmosphere. After 8 h the mixture was concentrate in vacuo, then purified by flash chromatography on silica using 2.5% methanol in dichloromethane to afford the allylamide, 17 (2.91 g, 52% yield). $^1$H NMR (200 MHz, CDCl$_3$) δ: 1.00 (m,6H), 1.90 (m,3H), 3.95 (m,2H), 4.79 (m,1H), 5.18 (m,2H), 5.81 (m,1H), 6.61 (t,1H), 8.76 (d,1H), 8.92(s,2H), 9.08 (s,1H).

Preparation of the Organosilane (Table 4, Compound 18):

Allylamide prepared in the manner described above for Compound 17, Table 4, (3.82 g) was dissolved in 15 mL dichloromethane and 15 mL dimethylchlorosilane. Chloroplatinic (20 mg) dissolved in a minimum amount of 2-propanol was added, and the resulting mixture was refluxed with stirring under a nitrogen atmosphere. Progress of the reaction was monitored by disappearance of starting material in quenched reaction aliquots (quenching solution was composed of 5 mL of absolute ethanol, 5 mL triethylamine and 5 mL diethyl ether). The assay procedure consisted of removing several drops of reaction mixture, evaporating to dryness under high vacuum to remove excess dimethylchlorosilane and adding several drops of quenching solution. The mixture was then heated for several minutes on an oil bath, diluted with dichloromethane, and examined by TLC. After about 2 h, TLC analysis of quenched reaction aliquots indicated complete consumption of starting material. Residual dimethylchlorosilane was removed by three successive additions and evaporations of small portions of dichloromethane. The quenching solution was then added, and the resulting mixture was refluxed for 30 min. under a nitrogen atmosphere. The mixture was filtered to remove triethylamine hydrochloride and evaporated to afford the crude ethoxyorganosilane which was purified by flash chromatography on silica using 10% acetonitrile in dichloromethane to afford the organosilane, 18, (3.97 g, 81% yield) as a tan powder. $^1$H NMR (200 MHz, CDCl$_3$) δ: 0.16 (s,6H), 0.61 (t,2H), 1.00 (m,6H), 1.21 (t,3H), 1.70 (m,5H), 3.30 (m,2H), 3.70 (q,2H), 4.62 (m,1H), 6.40 (t,1H), 8.20 (d,1H), 8.92 (d,2H), 9.14 (t,1H).

Preparation of the Stationary Phase, CSP-3:

Silica gel (3.0 g, Regis Rexchrom, 5μ, 100A) was placed in a 100 mL round bottom flask fitted with a boiling stick, Dean-Stark trap, and condenser. Benzene (35 mL) was added, and the mixture was heated at reflux for several hours. Dimethylformamide (1 mL) was then added to the benzene slurry, and the sample was evaporated to near dryness on a rotary evaporator. A dichloromethane solution of the organosilane 18 (0.77 g) was then added, and the resulting slurry was sonicated for several minutes, then evaporated to near dryness. The sample was again slurried in dichloromethane, sonicated, and evaporated to near dryness, this sequence being repeated several times to insure complete coverage of the silica gel. The nearly dry silica gel-silane mixture was then heated with rocking on a Kügelrohr distillation apparatus (120° C., 1 torr, 18 h). The silica gel was then slurried in ethanol, filtered through a fine sintered glass funnel, and washed repeatedly with ethanol and then methanol. (Analysis of the ethanol washes by chiral HPLC revealed that the unbonded silane had undergone no decomposition or racemization during the course of the bonding reaction). The washed silica gel was then slurried in methanol and packed into a 4.0 mm I.D.×14.5 cm length stainless steel HPLC column using an air driven Haskell pump operating at about 9000 psi. Recovered excess stationary phase from the column packer was dried thoroughly under high vacuum; elemental analysis (C 5.46%) indicated a loading of $2.5 \times 10^{-4}$ moles of selector per gram of stationary phase. Residual silanols on the chromatographic support were "endcapped" by passing a solution of 1 mL hexamethyldisilazane dissolved in 50 mL dichloromethane through the dichloromethane equilibrated column at a flow rate of 1 mL/min. The column was then sequentially eluted with dichloromethane, methanol and 20% 2-propanol in hexane.

PREPARATION OF CSP-4

The synthetic route for the preparation of CSP-4, which contained as an active portion, a chiral selector of the present invention, is shown in Table 5, below.

TABLE 5

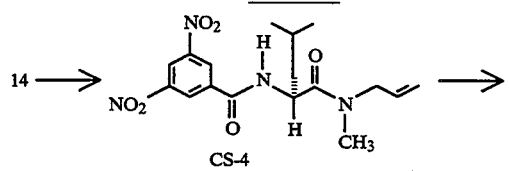

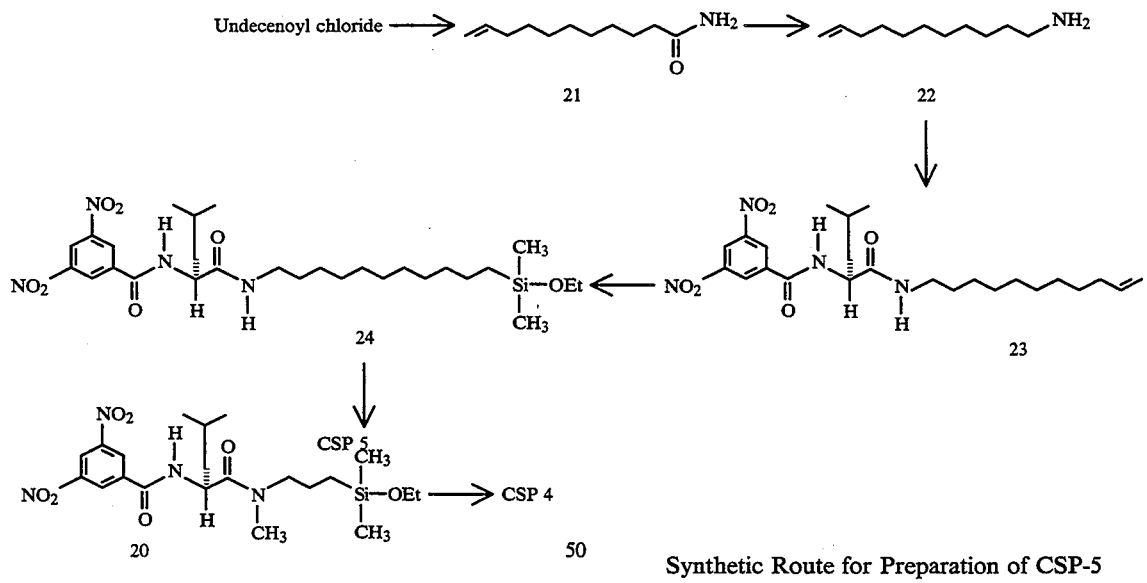

Synthetic Route for Preparation of CSP-4

Preparation of the CS-4:

3,5-dinitrobenzoyl-(S)-leucine, prepared as described in the procedure for CSP-1 supra (4.50 g) was dissolved in 100 mL dry tetrahydrofuran and stirred at 0° C. under a nitrogen atmosphere. EEDQ (3.42 g) was added and the resulting solution was stirred for 1 h. N-Methyl allylamine (0.98 g) was added, and the reaction mixture was gradually allowed to warm to room temperature while stirring for 8 h. The reaction mixture was then evaporated to dryness and purified by flash chromatography on silica using 4% acetonitrile in dichloromethane to afford CS-4 (2.72 g, 52% yield) as a white solid. $^1$H NMR (200 MHz, CDCl$_3$) δ: 1.02 (m,6H), 1.85 (m,3H), 3.06 (s) and 3.16 (s) (3H), 3.91 (dd) and 4.35 (dd) (2H), 4.11 (d,1H), 5.20 (m,2H), 5.85 (m,1H), 8.72 (bs,1H), 8.89 (m,2H), 9.11 (m,1H).

Preparation of the Organosilane (Table 5, Compound 20):

CS-4 (1.70 g) was converted to the corresponding organosilane, 20, using the hydrosilation procedure reported for the preparation of the organosilane, 18, in CSP-3 supra. Purification by flash chromatography on silica gel using 10% acetonitrile in dichloromethane afforded the organosilane 20 as a foam (790 mg, 36% yield). $^1$H NMR (200 MHz, CDCl$_3$) δ: 0.18 (m,6H), 0.60 (m,2H), 1.01 (m,6H), 1.21 (m,3H), 1.55 (m,2H), 1.82 (m,3H), 3.07 (s) and 3.19 (s) (3H), 3.42 (m) and 3.70 (m) (2H), 3.65 (m,2H), 5.15 (m,1H), 8.81 (m,2H), 9.01 (m, 1H), 9.07 (m,1H).

Preparation of stationary Phase, CSP-4:

Bonding of the organosilane 20 (790 mg) to silica gel to afford CSP-4 followed the procedure reported for the preparation of the stationary phase CSP-3 supra. Stationary phase removed from the column packer indicated (C 4.58%) a loading of $2.0 \times 10^{-4}$ moles of selector per gram of stationary phase.

PREPARATION OF CSP-5

The synthetic route for the preparation of CSP-5, which may be commercially obtained from Regis Chemical Company, Morton Grove, Ill., is shown in Table 6, below.

Synthetic Route for Preparation of CSP-5

Preparation of amide 21 (Table 6):

10-undecen-1-oy chloride (50 g) was placed in a round bottom flask with 300 mL dichloromethane. Concentrated ammonium hydroxide solution (65 mL) was then added, and the resulting solution was stirred vigorously for 2 h. The two phase mixture was then separated using a separatory funnel. The organic layer was washed with water and then brine, then dried over anhydrous magnesium sulfate. Evaporation afforded amide 21 which was used without further purification or characterization.

Preparation of amine 22 (Table 6):

Amide 21 (6.2 g) was dissolved in 120 mL dry THF. LiAlH$_4$ (2.0 g) was then added and the resulting mixture was refluxed for 2 h under a nitrogen atmosphere. Excess LiAlH$_4$ was then carefully quenched by addition of 200 mL of water. The resulting solution was extracted three times with 50 mL diethyl ether, the combined ether extracts were washed with brine, then dried over anhydrous magnesium sulfate. Evaporation of the ether layer afforded crude amine 22 which was used without further purification of characterization.

Preparation of amide 23 (Table 6):

3,5-dinitrobenzoyl-(S)-leucine, prepared as described in the procedure for CSP-1 Supra (5.0 g) was dissolved in 100 mL tetrahydrofuran and chilled with stirring on an ice bath. EEDQ (3.8 g) was added and the mixture was stirred under a nitrogen atmosphere for 45 min. Amine 22 (2.6 g) was then added via syringe and the resulting mixture was allowed to gradually warm to room temperature while stirring for 8 h. The reaction mixture was then evaporated to dryness and purified by flash chromatography on silica using 2.5% methanol in dichloromethane to afford amide 23 (4.5 g, 62% yield) as a white solid. $^1$H NMR (200 MHz, CDCl$_3$) δ: 0.99 (m,6H), 1.30 (bs, 12H), 1.51 (m,2H), 1.80 (m,3H), 2.03 (m,2H), 3.19 (m,1H), 3.3.9 (m, 1H), 4.64 (m,1H), 4.95 (m,2H), 5.81 (m,1H), 6.22 (m,2H), 8.42 (d,1H), 8.91 (s,2H), 9.12 (s,1H).

Preparation of the Organosilane 24 (Table 6):

Amide 23 (4.50 g) was converted to the corresponding organosilane 24 using the hydrosilylation procedure reported in the preparation of the organosilane 18 described in the procedure for CSP-3. Purification by flash chromatography on silica gel using 5% acetonitrile in dichloromethane afforded the organosilane 24 (1.90 g, 35% yield) as a yellow waxy solid. $^1$H NMR (200 MHz, CDCl$_3$) δ: 0.08 (s,6H), 0.58 (t,2H), 0.99 (m,6H), 1.20 (t,3H), 1.30 (m,16H), 1.50 (m,2H), 1.75 (m,3H), 3.19 (m, 1H), 3.39 (m,1H), 3.65 (q,2H), 4.64 (m,1H), 6.28 (bs,1H), 8.49 (bs,1H), 8.95 (s,2H), 9.10 (s,1H).

Preparation of the Stationary Phase CSP-5:

Bonding of the organosilane 24 (1.90 g) to silica gel to afford CSP-5 followed the procedure reported for the preparation of the stationary phase CSP-3 supra. Stationary phase removed from the column packer indicated (c 5.89%) a loading of 1.9×10$^{-4}$ moles of selector per gram of stationary phase.

PREPARATION OF CSP-6

The synthetic route for the preparation of CSP-6, using a chiral selector, CS-6, of the present invention is shown in Table 7, below.

Synthetic Route for Preparation of CSP-6

Preparation of amide 25 (Table 7):

Amide 25 was prepared using a procedure analogous to the preparation of amide 21 described in the procedure for CSP-5 supra, except that a 30% aqueous solution of methylamine was used in place of a concentrated ammonium hydroxide solution.

Preparation of amine 26 (Table 7):

Reduction of amide 25 to afford amine 26 followed the procedure described for the preparation of amine 22 as described for CSP-5 supra. A small amount of amine was purified by vacuum distillation with the product being obtained as a clear liquid 91°–95° C. at 0.1 torr.

Preparation of CS-6:

3,5-dinitrobenzoyl-(S)-leucine, prepared as described in the procedure for CSP-1 supra, (5.0 g) was dissolved in 100 mL tetrahydrofuran and chilled with stirring on an ice bath. EEDQ (3.8 g) was added and the mixture was stirred under a nitrogen atmosphere for 45 min. Amine 26 (2.6 g) was added via syringe and the resulting mixture was allowed to gradually warm to room temperature while stirring for 8 h. The reaction mixture was evaporated to dryness and purified by flash chromatography on silica using 2.5% methanol in dichloromethane to afford CS-6 (3.66 g, 49% yield) as a yellow oil. $^1$H NMR (200 MHz, CDCl$_3$) δ: 1.00 (m,6H), 1.30 (m,14H), 1.82 (m,3H), 2.03 (m,2H), 3.09 (s) and 3.19 (s) (3H), 3.81 (m,1H), 4.16 (m,1H), 4.98 (m,2H), 5.18 (m,1H), 5.80 (m,1H), 8.81 (d,1H), 8.86 (d,1H), 9.07 (m,1H).

Preparation of the Organosilane 28 (Table 7):

CS-6 (3.00 g) was converted to the corresponding organosilane 28 using the hydrosilylation procedure reported for the preparation of the organosilane 18 in CSP-3 supra. Purification by flash chromatography on silica gel using 5% acetonitrile in dichloromethane afforded the organosilane 28 (0.68 g, 35% yield). $^1$H NMR (200 MHz, CDCl$_3$) δ: 0.10 (s,6H), 0.57 (m,2H), 0.99 (m,6H), 1.19 (t,3H), 1.30 (m,18H), 1.65 (m,3H), 2.99 (s) and 3.12 (s) (3H), 3.21 (m,2H), 3.68 (q,2H), 5.18 (m,1H), 7.73 (m,1H), 8.94 (m,2H), 9.16 (m,1H).

Preparation of Stationary Phase CSP-6:

Bonding of the organosilane 28 (0.68 g) to silica gel to afford CSP-6 followed the procedure reported for the preparation of the stationary phase CSP-3 supra. Sta-

TABLE 7

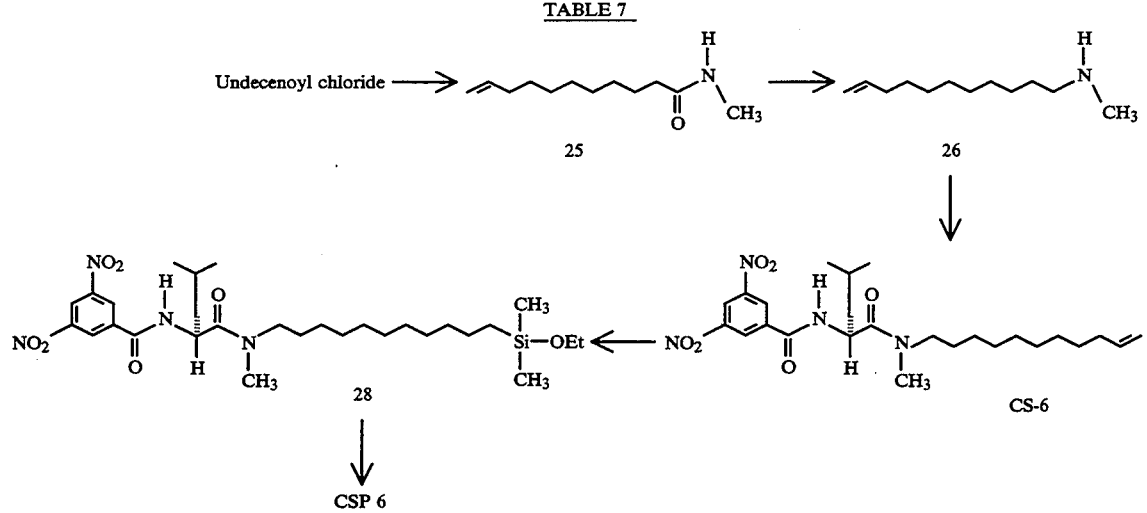

tionary phase removed from the column packer indicated (C 5.85%) a loading of $1.8 \times 10^{-4}$ moles of selector per gram of stationary phase.

PREPARATION OF CSP-7

The synthetic route for the preparation of CSP-7, using a chiral selector, CS-7, of the present invention, both arms of which were immobilized to a silica support using a monofunctional linkage as contemplated by the present invention, is shown in Table 8, below.

TABLE 8

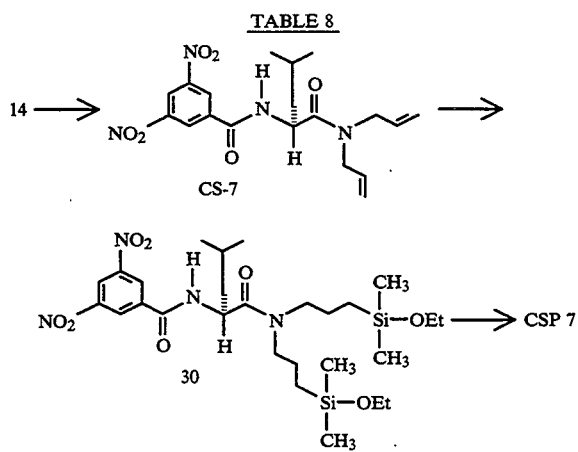

Synthetic route for preparation of CSP-7

Preparation of CS-7:

3,5-dinitrobenzoyl-(S)-leucine, prepared as described in the procedure for CSP-1 supra (3.15 g) was dissolved in 100 mL of dry tetrahydrofuran and chilled with stirring on an ice bath. EEDQ (2.39 g) was added and the mixture was stirred under a nitrogen atmosphere for 45 min. Diallylamine (0.94 g) was then added via syringe and the resulting mixture was allowed to gradually warm to room temperature while stirring for 8 h. The reaction mixture was evaporated to dryness and purified by flash chromatography on silica using 1.5% methanol in dichloromethane to afford CS-7 (1.40 g, 36% yield) as a yellowish solid. $^1$H NMR (200 MHz, CDCl$_3$) δ: 1.00 (m,6H), 1.85 (m,3H), 3.80 (m,1H), 4.03 (m,2H), 4.51 (m,1H), 5.12 (m,4H), 5.90 (m,2H), 8.90 (d,2H), 8.96 (d,2H), 9.10 (t,1H).

Preparation of the Organosilane 30 (Table 8):

CS-7 (1.40 g) was converted to the corresponding organosilane 30 using the hydrosilylation procedure reported for the preparation of the organosilane 18 in CSP-3 supra. Purification by flash chromatography on silica gel using 5% acetonitrile in dichloromethane afforded the organosilane 30 (1.32 g, 62% yield). $^1$H NMR (200 MHz, CDCl$_3$) δ: 0.10 (s,12H), 0.60 (m,4H), 0.99 (m,6H), 1.20 (m,6H), 1.42 (m,2H), 1.60 (m,2H), 1.80 (m,3H), 3.01 (m,1H), 3.30 (m,1H), 3.39 (m,1H), 3.70 (m,4H), 3.83 (m,1H), 5.15 (t,1H), 8.68 (d,1H), 8.82 (s,2H), 9.06 (s,1H).

Preparation of Stationary Phase CSP-7:

Bonding of the organosilane 30 (0.60 g) to silica gel to afford CSP-7 followed the procedure reported for the preparation of stationary phase CSP-3 supra. Stationary phase removed from the column packer indicated (C 5.06%) a loading of $1.8 \times 10^{-4}$ moles of selector per gram of stationary phase.

PREPARATION OF CSP-9

The synthetic route for the preparation of CSP-9, using a chiral selector, CS-9, of the present invention is shown in Table 9, below.

TABLE 9

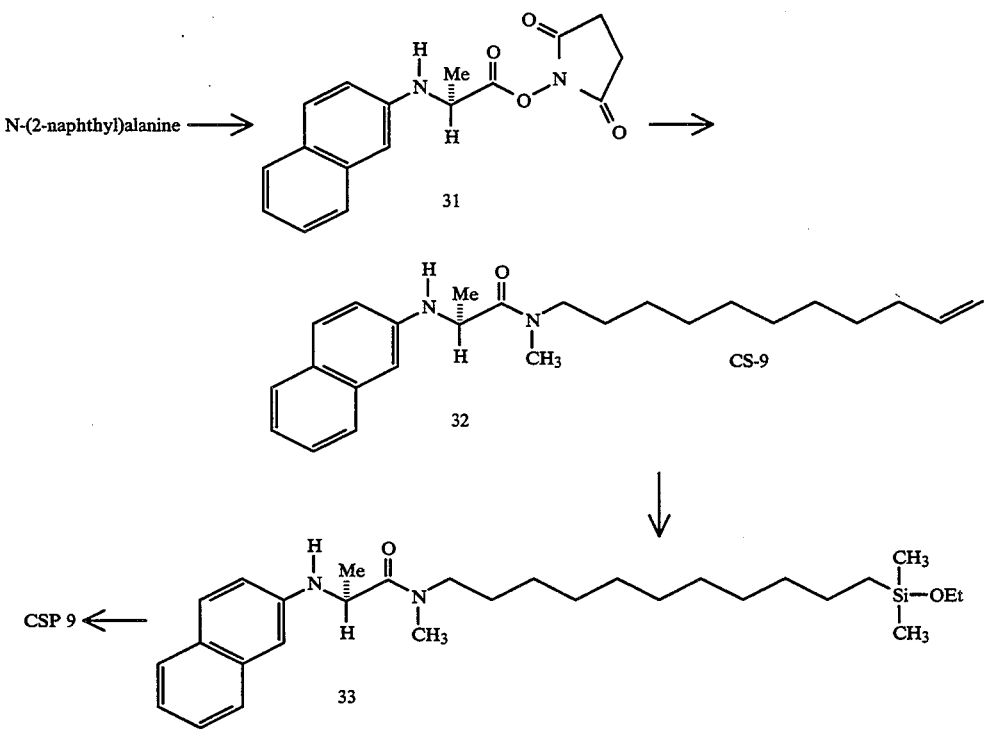

Synthetic Route for Preparation of CSP-9

Preparation of Active Ester 31 (Table 9):

Racemic N-(2-naphthyl)alanine (17.1 g) was prepared according to the method described by Pirkle, et al. in *J. Org. Chem.*, 51, 102 (1986), the contents of which are incorporated herein by reference, and was placed in a round bottom flask fitted with a magnetic stirrer and a nitrogen inlet. Dimethylformamide (300 mL), N-hydroxysuccinimide (9.15 g) and dicyclohexylcarbodiimide (18.0 g) were added and the reaction mixture was stirred for 8 h at room temperature. Stirring was then discontinued, and precipitated dicyclohexylurea (DCU) was allowed to aggregate. The reaction mixture was filtered and evaporated to dryness under reduced pressure. The resulting red oily solid was purified by flash chromatography on silica to afford active ester 31 (21.0 g, 85% yield) as a pale yellow powder. $^1$H NMR (200 MHz, CDCl$_3$) δ: 1.78 (d,3H), 2.77 (s,4H), 4.21 (d,1H), 4.59 (m,1H), 6.92 (m,2H), 7.23 (m,2H), 7.38 (m,1H), 6.78 (m,1H), 6.92 (m,1H), 7.20 (m,1H), 7.33 (m, 1H), 7.65 (m,3H).

preparation of CS-9:

Racemic active ester 31 (3.0 g) was dissolved in 50 mL dimethylformamide and stirred at room temperature under a nitrogen atmosphere. Amine 26, prepared as described in the procedure for CSP-6 supra (1.76 g) was added slowly via syringe and the resulting solution was stirred for 10 h, then evaporated to dryness under reduced pressure. The crude product was purified by flash chromatography on silica using 10% acetonitrile in dichloromethane to afford CS-9 as a pale yellow solid (3.05 g, 84% yield). $^1$H NMR (200 MHz, CDCl$_3$) δ: 1.21 (bs,14H), 1.39 (d,3H), 2.00 (m,2H), 2.96 (s) and 3.06 (s) (3H), 3.40 (m,2H), 4.55 (1,1H), 4.96 (m,2H), 5.80 (m, 1H), 6.78 (m,1H), 6.94 (m,1H), 7.20 (m,1H), 7.36 (m,1H), 7.69 (m,4H).

Chromatographic Resolution of the Enantiomers of CS-9:

The enantiomers of CS-9 were preparatively resolved on a 2.5 cm I.D.×90 cm length column containing (S) CSP 1 using a 2:1:7 mixture of 2-propanol/dichloromethane/hexane as mobile phase. The second eluting (S) enantiomer of CS-9 was obtained as a pale yellow solid (1.27 g, 85% recovery) which showed no traces of the minor enantiomer by HPLC analysis.

Preparation of the (S)-Organosilane 33 (Table 9):

The (S) enantiomer of CS-9 (0.98 g) was converted to the corresponding organosilane 33 using the hydrosilylation procedure reported for the preparation of the organosilane 18 in CSP-3 supra. Purification by flash chromatography on silica gel using 20% acetonitrile in dichloromethane afford the (S) organosilane, 33. $^1$H NMR (200 MHz, CDCl$_3$) δ: 0.11 (s,6H), 0.58 (t,2H), 0.99 (t,3H), 1.26 (m,18H), 1.40 (d,3H), 2.96 (s) and 3.10 (s) (3H), 3.40 (m,2H), 3.66 (q,2H), 4.60 (m, 1H), 6.76 (m,1H), 6.90 (m,2H), 7.16 (m,1H), 7.35 (m, 1H), 7.69 (m,3H).

preparation of stationary Phase CSP-9:

Bonding of the (S)-organosilane 33 to silica gel to afford CSP-9 followed the procedure reported for the preparation of stationary phase CSP-3 supra. Stationary phase removed from the column packer indicated (C 7.75%) a loading of 2.5×10$^{-4}$ moles of selector per gram of stationary phase.

Chromatographic Evaluation

A homologous series of carbameate derivatives of amino acids were employed as analytes to evaluate the chromatographic performance of CSP's 1-7.

The analytes were derived from n-alkyl carbamate derivatives of the 3,5-dimethylanilide of leucine shown in Table 10, below.

TABLE 10

Leucine 3,5 Dimethylanilide Alkyl Carbamate Series, n=1, 2, 4, 6, 8, 10, 12, 14.

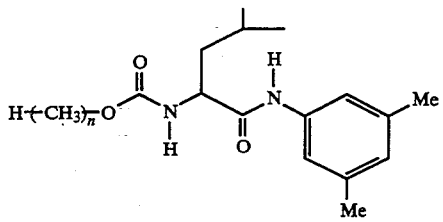

The performance of CSP-1 and CSP-2 in chromatographically separating the enantiomers of the alkyl carbamate analytes of Table 10 is shown in FIG. 1. As seen in FIG. 1, the chromatographic separation faction, α, is greater on CSP-2 which utilized a chiral selector of the present invention, rather than the commercially available CSP-2; this was true even though CSP-2 was immobilized to silica via a multifunctional linkage. Further, CSP-2 was found to afford reduced retention and improved bandshapes for the separations shown in FIG. 1.

Figure 2:
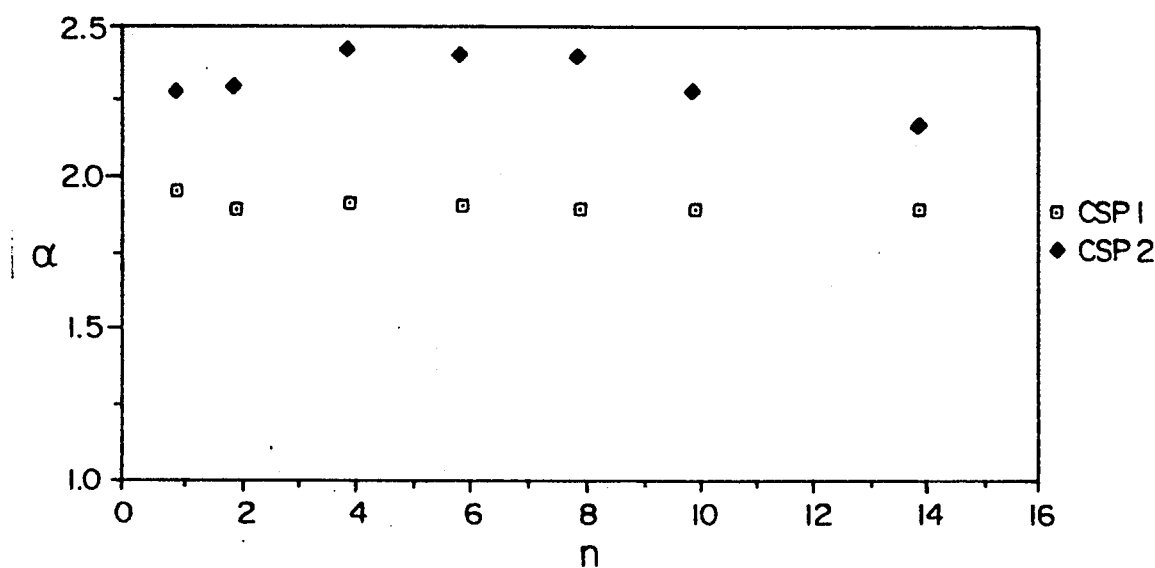
FIG. 2 is a graph showing the reverse phase separation of the enantiomers of a series of alkyl carbameate derivatives of leucine 3,5-dimethylanilide using a preferred chiral selector of the present invention as compared to a commercially available chiral selector.

A reversed-phase chromatographic analysis of leucine 3,5-dimethylanilide alkyl carbamate series of Table 10 was performed on CSP-1 and CSP-2; the results are shown in FIG. 2. As seen from FIG. 2, CSP-2, which utilizes, as an active portion, a chiral selector of the present invention, evinced superior chromatographic separation factors, α, relative to commercially available CSP-1.

Figure 3:
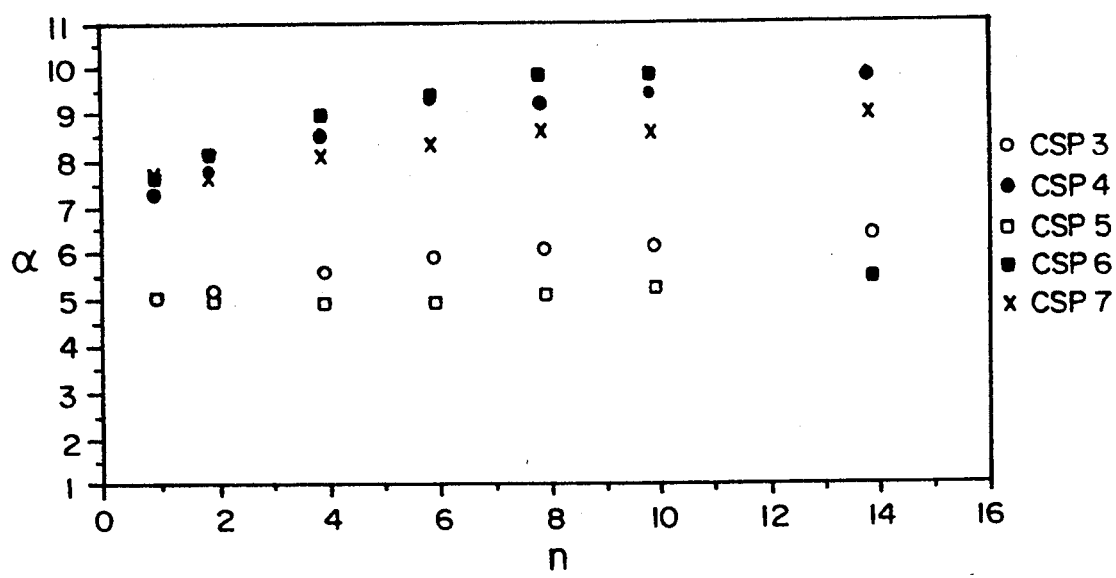
FIG. 3 is a graph showing the normal phase separation of the enantiomers of a series of alkyl carbameate derivatives of leucine 3,5-dimethylanilide and the influence thereon of tether length, number of tethers and the presence of a monofunctional silane linkage using several analogs of a preferred chiral selector of the present invention employed as a chiral stationary phase in a liquid chromatographic column.

Normal phase separation of the enantiomers of the leucine 3,5-dimethylanilide alkyl carbamate series of Table 10 was performed on CSP-3 and CSP-4, to compare the effect of a monofunctional linkage as contemplated by the present invention on a stationary phase that employs as an active portion a commercially available chiral selector (CSP-3), and on a chiral stationary phase formed from a chiral selector of the invention (CSP-4). The results are shown in FIG. 3. As seen in FIG. 3, the separation factor, α, afforded by CSP-4 was superior to that of CSP-3. Moreover, a comparison of the normal phase separation obtained by CSP-3, which used a conventional chiral selector but employed a monofunctional linkage of the present invention, to CSP-1, as shown in FIG. 1, which employed the same chiral selector as CSP-3 but which utilized the conventional multifunctional linkage, showed that the separation achieved by CSP-3 was greater than that of CSP-1.

Normal phase separation of the enantiomers of the leucine 3,5-dimethylanilide alkyl carbamate series of Table 10 was performed on CSP-5 and CSP-6 to investigate the effect of tether length on chromatographic behavior when a monofunctional linkage of the type contemplated by the present invention is used. CSP-5 employed the same commercially available chiral selector portion as CSP-1 and CSP-3, only CSP-5 was immobilized to silica by way of an eleven carbon tether through a monofunctional linkage; CSP-6 utilized both a chiral selector and monofunctional linkage of the present invention, as well as an eleven carbon tether to silica. The results are shown in FIG. 3. As shown in FIG. 3, CSP-6 afforded greater separation than did CSP-5. Also as can be seen from FIG. 3, CSP-3, which was analogous to CSP-5 but for the fact that CSP-3 employed a three carbon tether as opposed to the eleven carbon tether of CSP-5, showed greater separation than CSP-5 which indicated that shorter tethers are preferable in the practice of the present invention.

Normal phase separation of the enantiomers of the leucine 3,5-dimethylanilide alkyl carbamate series of Table 10 was also performed on CSP-7, which utilized a chiral selector of the present invention which was immobilized to silica by two arms, each via monofunctional linkages of the invention. The results are shown in FIG. 3. As can be seen in FIG. 3, CSP-7 showed superior separation, as compared with CSP-3 and CSP-5, each of which employed a conventional chiral selector portion. CSP-7 showed superior separation even though CSP-3 and CSP-5 both utilized a monofunctional linkage as contemplated by the invention.

Figure 4:
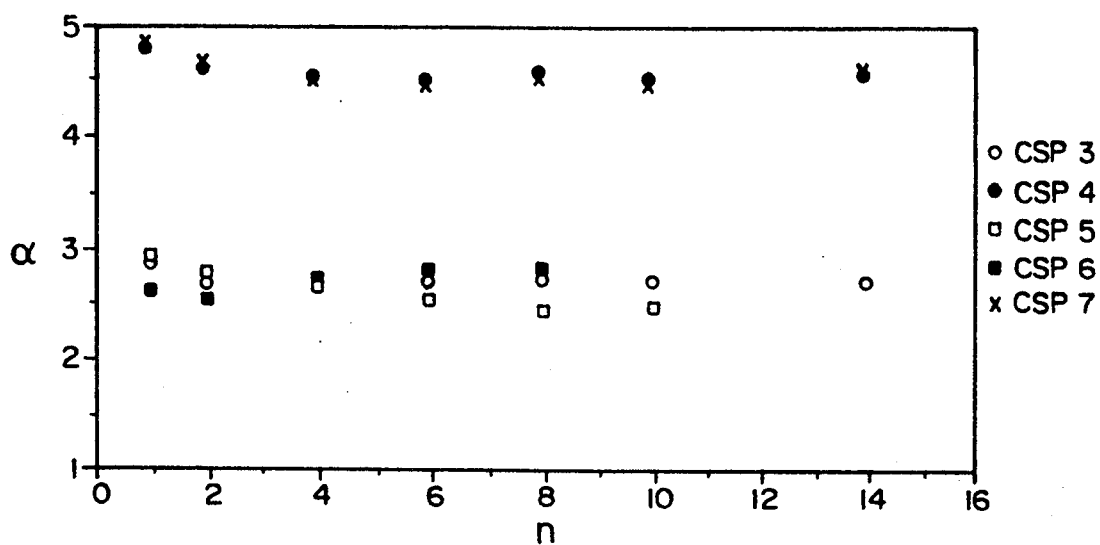
FIG. 4 is a graph showing the reverse phase separation of the enantiomers of a series of alkyl carbameate derivatives of leucine 3,5-dimethylanilide and the influence thereon of tether length, number of tethers and the presence of a monofunctional silane linkage using several analogs of a preferred chiral selector of the present invention employed as a chiral stationary phase in a liquid chromatographic columns.

A reversed-phase chromatographic analysis of the leucine 3,5-dimethylanilide alkyl carbamate series of Table 10 was performed with CSP-3, CSP-4, CSP-5, CSP-6 and CSP-7. The results are shown in FIG. 4. As seen from FIG. 4, the data obtained for the reversed phase separation using these CSP's are similar to that obtained for the normal phase separation shown in FIG. 3. The performance of CSP-6, which contained an eleven carbon linkage to the silica support, was, however, no longer comparable to that of the other N-methylated CSP's, namely CSP-4 and CSP-7. The diminished separation factors observed for CSP-6 in this regard are believed to be a result of non-specific hydrophobic adsorption arising from the long chain of CSP-6, which result is supported by the relatively long retention times observed for CSP-6.

Chromatographic separation of enantiomers of various 3,5-dinitrobenzoyl leucine amides was also conducted using the N-(2-naphthyl)alanine chiral stationary phase, CSP-8, as commercially available from Regis Chemical Company, Morton Grove, Ill., and compared to the separation achieved using CSP-9, which utilized as an active portion, a chiral selector of the present invention, and which was immobilized to silica via a monofunctional linkage of the invention. The 3,5-dinitrobenzoyl leucine amides that were used and the results obtain are shown in Table 11, below.

TABLE 11

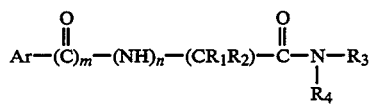

| | CSP 8 | | | CSP 9 | | |
|---|---|---|---|---|---|---|
| R | $k'_1$ | $k'_2$ | α | $k'_1$ | $k'_2$ | α |
| n-tetradecyl | 1.35 | 17.45 | 12.93 | 1.07 | 33.72 | 31.51 |
| t-butyl | 0.76 | 7.83 | 10.30 | 1.22 | 32.81 | 26.89 |
| adamantyl | 0.86 | 9.62 | 11.19 | 1.63 | 45.72 | 28.05 |

Separation of the enantiomers of three 3,5-dinitrobenzoyl leucine amides on CSP-8 and CSP-9. Conditions: flow rate=2.0 mL/min.; mobile phase=20% 2-propanol in hexane.

As seen from Table 11, CSP-9 which utilized as an active portion a chiral selector of the present invention achieved superior separations in all cases than did CSP-8. In addition to showing increased enantioselectivity, CSP-9 may also show enhanced stability, especially in reversed-phase application; this is because amide linkages, as present in CSP-9, are known to be more stable toward hydrolytic cleavage than ester linkages, as present in CSP-8.

Chromatographic separation of various 3,5-dinitrobenzoyl β-amino esters was conducted on CSP-11 and CSP-12 both formed in accordance with the present invention. The esters used and the conditions employed, are shown in Table 12, below.

TABLE 12

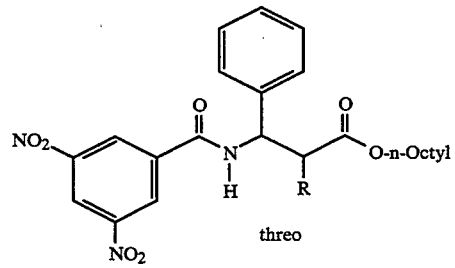

| | CSP 11 | | | CSP 12 | | |
|---|---|---|---|---|---|---|
| R | $k'_1$ | $k'_2$ | α | $k'_1$ | $k'_2$ | α |
| Et | 7.63 | 11.41 | 1.50 | 4.19 | 7.36 | 1.76 |
| i-Pr | 7.70 | 14.59 | 1.89 | 4.31 | 8.88 | 2.06 |
| t-Bu | 4.40 | 16.23 | 3.69 | 2.63 | 12.35 | 4.69 |

Separation of the enantiomers of some 3,5-DNB β-amino esters on three naproxen-derived CSP's. Conditions: flow rate=2.0 mL/min; mobile phase=20% 2-propanol in hexane.

As seen from Table 12, excellent separation of these ester analytes was achieved with both CSP-11 and CSP-12 each of which employed as an active portion a chiral selector o of the present invention, with CSP-12 further employing a monofunctional silane linkage as contemplated by the invention.

What is claimed is:

1. A chromatographic column having a stationary phase wherein said stationary phase comprises a compound having the formula:

$$Ar-(C)_m-(NH)_n-(CR_1R_2)-\overset{O}{\underset{}{C}}-\overset{R_4}{\underset{R_3}{N}}$$

wherein
Ar is a monocyclic or ortho-fused polycyclic aromatic moiety having up to 10 ring carbon atoms, either of which may be unsubstituted or substituted with one or more $C_1$ to $C_6$ alkyl, $C_1$ to $C_6$ alkoxy, $NO_2$, $N(R_5)_3^+$, $CN$, $COOR_6$, $SO_3H$ and $COR_7$ groups wherein $R_5$, $R_6$ and $R_7$ are each independently hydrogen or $C_1$ to $C_6$ alkyl;

$R_1$ and $R_2$ are each independently hydrogen, $C_1$ to $C_6$ alkyl or phenyl;

$R_3$ and $R_4$ are each independently $C_1$ to $C_{12}$ alkyl or $C_2$ to $C_{12}$ alkenyl; and m and n are each independently 1 or 0, said compound being an R or an S enantiomer or a mixture of R and S enantiomers immobilized on a support effective for use in chromatographic separations.

2. The column of claim 1 wherein said support is silica or alumina.

3. The column of claim 2 wherein said compound is immobilized on silica via at least one monofunctional silane linkage.

4. The column of claim 3 wherein said stationary phase has the formula:

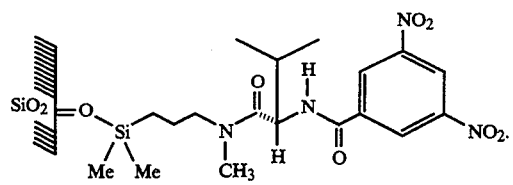

5. The column of claim 3 wherein said stationary phase has the formula:

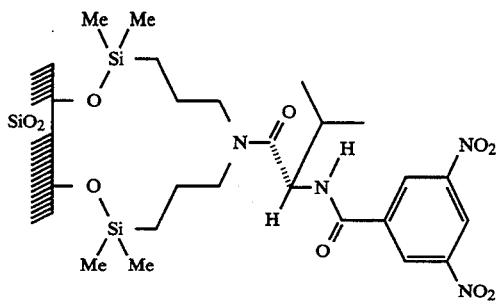

6. The column of claim 3 wherein said stationary phase has the formula:

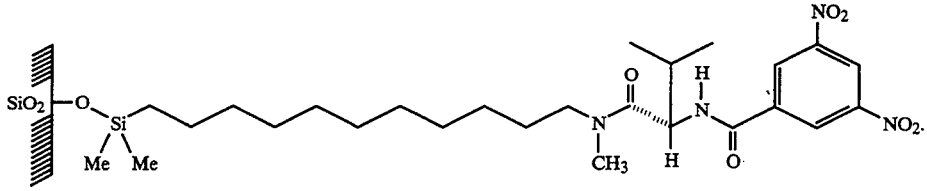

7. The column of claim 3 wherein said stationary phase has the formula:

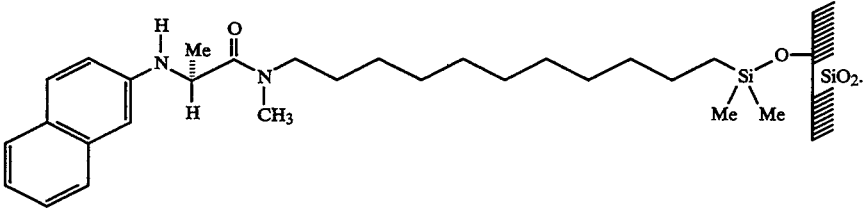

8. The column of claim 3 wherein said stationary phase has the formula:

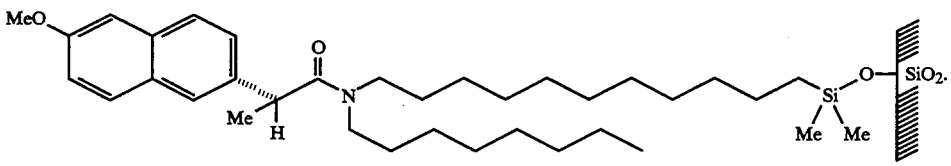

9. The column of claim 2 wherein said stationary phase has the formula:

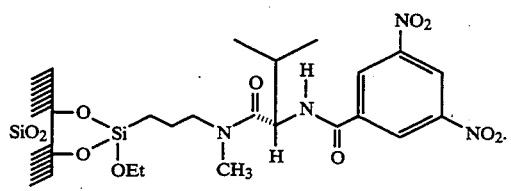

10. The column of claim 2 wherein said stationary phase has the formula:

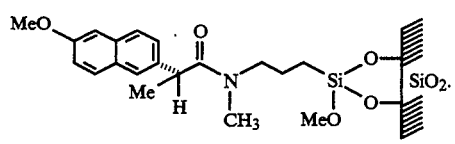

11. An improved chromatographic column of the type containing a derivative of a 3,5-dinitrobenzoyl phenylglycine, 3,5-dinitrobenzoyl leucine, a naphthylleucine or a naphthylalanine wherein said derivative is immobilized on a silica support to form a stationary phase suitable for chromatographic separation wherein the improvement comprises a connecting tether formed of a secondary amine to connect said derivative to said silica support.

12. An improved chromatographic column of the type containing a phase of the formula:

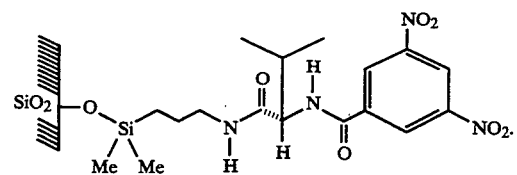

* * * * *

UNITED STATES PATENT AND TRADEMARK OFFICE
CERTIFICATE OF CORRECTION

PATENT NO.  : 5,422,004
DATED       : June 6, 1995
INVENTOR(S) : William H. Pirkle, et al.

It is certified that error appears in the above-indentified patent and that said Letters Patent is hereby corrected as shown below:

On the Title Page, Section [56], under "OTHER PUBLICATIONS", Column 2, line 4: "Functionally" should read --Functionality--

On the Title Page, Section [56], Column 3, line 24: "478" should read --479--

On the Title Page, Section [56], Column 3, lines 35-36: "Conformation" should read --Conformational--

On the Title Page, Section [56], Column 4, line 5: after "82-89," insert --92,--

On the Title Page, Section [56], Column 4, line 35: "Prikle" should read --Pirkle--

On the Title Page, Section [56], Column 4, line 39: "Advance" should read --Advances--

Column 3, line 34: "K-electron" should read -- π-electron --

Column 3, line 44: "17,991," should read --17, 1991--

UNITED STATES PATENT AND TRADEMARK OFFICE
CERTIFICATE OF CORRECTION

PATENT NO. : 5,422,004
DATED : June 6, 1995
INVENTOR(S) : William H. Pirkle, et al.

It is certified that error appears in the above-indentified patent and that said Letters Patent is hereby corrected as shown below:

Column 6, line 2: after "methyl," insert -- $C_1$.--
Column 6, line 61: " $R_{12}$ " should read -- $R_1$ --
Column 7, line 32: " 5-naphthyl " should read -- ß-naphthyl --
Column 7, line 47: after "of" delete --,--

Column 10, line 60: " $R_{(}$ " should read -- $R_9$ --
Column 15, line 45: after "ppm" insert --(δ)--
Column 15, line 49: delete "A"
Column 18, line 6: "8.92(s,2H)" should read --8.92 (s,2H)--
Column 18, line 12: after "Chloroplatinic" insert --acid--

UNITED STATES PATENT AND TRADEMARK OFFICE
CERTIFICATE OF CORRECTION

PATENT NO. : 5,422,004
DATED : June 6, 1995
INVENTOR(S) : William H. Pirkle, et al.

It is certified that error appears in the above-indentified patent and that said Letters Patent is hereby corrected as shown below:

Column 18, line 43: "100A)" should read --100Å)--
Column 20, line 16: "stationary" should read --Stationary--
Column 21, line 20: "3.3.9" should read --3.39--
Column 25, line 20: "preparation" should read --Preparation--
Column 25, line 57: "preparation of stationary" should read --Preparation of Stationary--
Column 27, lines 51-59, Table 11:
"                                "

TABLE 11

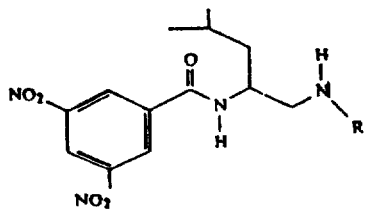

UNITED STATES PATENT AND TRADEMARK OFFICE
CERTIFICATE OF CORRECTION

PATENT NO. : 5,422,904
DATED : June 6, 1995
INVENTOR(S) : William H. Pirkle, et al.

It is certified that error appears in the above-indentified patent and that said Letters Patent is hereby corrected as shown below:

should read -- TABLE 11

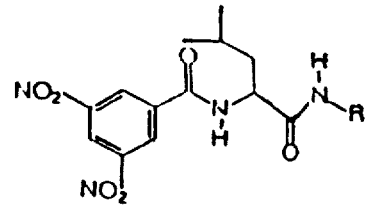

--

Column 28, line 44: after "selector" delete --o--

Signed and Sealed this

Eleventh Day of June, 1996

*Attest:*

BRUCE LEHMAN

*Attesting Officer*   Commissioner of Patents and Trademarks